US006667313B1

(12) United States Patent
Hamann et al.

(10) Patent No.: US 6,667,313 B1
(45) Date of Patent: Dec. 23, 2003

(54) 8-SUBSTITUTED-6-TRIFLOUROMETHYL-9-PYRIDO [3,2-G] QUINOLINE COMPOUNDS AS ANDROGEN RECEPTOR MODULATORS

(75) Inventors: Lawrence G. Hamann, Cherry Hill, NJ (US); James Kong, San Diego, CA (US); James P. Edwards, San Diego, CA (US)

(73) Assignee: Ligand Pharmaceuticals Inc., San Diego, CA (US)

( * ) Notice: Subject to any disclaimer, the term of this patent is extended or adjusted under 35 U.S.C. 154(b) by 0 days.

(21) Appl. No.: 09/648,683

(22) Filed: Aug. 25, 2000

Related U.S. Application Data
(60) Provisional application No. 60/151,235, filed on Aug. 27, 1999.

(51) Int. Cl.[7] .................... A61K 31/44; C07D 471/04
(52) U.S. Cl. ............................ 514/292; 546/88
(58) Field of Search ........................ 546/88; 514/292

(56) References Cited

U.S. PATENT DOCUMENTS

| | | | |
|---|---|---|---|
| 3,775,332 A | 11/1973 | Heins et al. | 252/95 |
| 3,798,031 A | 3/1974 | Janssens et al. | 96/1.8 |
| 3,830,647 A | 8/1974 | Janssens et al. | 96/1.5 |
| 3,832,171 A | 8/1974 | Janssens et al. | 96/1.5 |
| 3,928,686 A | 12/1975 | Poot et al. | 428/457 |
| 3,936,461 A | 2/1976 | Schwender et al. | 260/298 |
| 3,979,394 A | 9/1976 | Janssens et al. | 260/283.82 |
| 3,993,656 A | 11/1976 | Rooney et al. | 260/296 N |
| 4,138,490 A | 2/1979 | Brittain et al. | 424/258 |
| 4,193,931 A | 3/1980 | Loeliger | 424/308 |
| 4,326,055 A | 4/1982 | Loeliger | 542/429 |
| 4,415,572 A | 11/1983 | Tominaga et al. | 424/250 |
| 4,427,654 A | 1/1984 | Austin | 424/95 |
| 4,505,852 A | 3/1985 | Rasnick et al. | 260/112.5 R |
| 4,534,979 A | 8/1985 | Loev et al. | 514/529 |
| 4,539,134 A | 9/1985 | Martin et al. | 252/156 |
| 4,578,498 A | 3/1986 | Frickel et al. | 560/8 |
| 4,710,507 A | 12/1987 | Campbell et al. | 514/312 |
| 4,728,653 A | 3/1988 | Campbell et al. | 514/312 |
| 4,801,733 A | 1/1989 | Wuest et al. | 560/56 |
| 4,831,052 A | 5/1989 | Shudo | 514/455 |
| 4,833,240 A | 5/1989 | Maignan et al. | 536/55.2 |
| 4,874,747 A | 10/1989 | Shroot et al. | 514/23 |
| 4,879,284 A | 11/1989 | Lang et al. | 514/62 |
| 4,898,864 A | 2/1990 | Maignan et al. | 514/237.5 |
| 4,925,979 A | 5/1990 | Shudo | 562/462 |
| 4,933,336 A | 6/1990 | Martin et al. | 514/222.5 |
| 4,943,502 A | 7/1990 | Terrell et al. | 430/58 |
| 4,981,784 A | 1/1991 | Evans et al. | 435/6 |
| 5,004,730 A | 4/1991 | Philippe et al. | 514/29 |
| 5,071,773 A | 12/1991 | Evans et al. | 436/501 |
| 5,081,242 A | 1/1992 | Combs | 544/52 |
| 5,091,528 A | 2/1992 | Gluchowski et al. | 544/105 |
| 5,124,473 A | 6/1992 | Shroot et al. | 560/56 |
| 5,147,844 A | 9/1992 | Weber et al. | 503/227 |

(List continued on next page.)

FOREIGN PATENT DOCUMENTS

| | | |
|---|---|---|
| DE | 21 11 938 | 10/1971 |
| DE | 26 11 824 | 9/1976 |
| DE | 38 10 706 | 10/1989 |
| EP | 0 272 910 | 6/1988 |
| EP | 0 356 230 | 2/1990 |
| EP | 0 542 609 | 5/1993 |
| EP | 0 718 285 | 6/1996 |
| GB | 2 058 788 | 4/1981 |
| SU | 555119 | 6/1977 |
| WO | 89/07441 | 8/1989 |
| WO | 93/21146 | 10/1993 |
| WO | 94/12880 | 6/1994 |
| WO | 94/15901 | 7/1994 |
| WO | 94/15902 | 7/1994 |
| WO | 94/17796 | 8/1994 |
| WO | 94/20093 | 9/1994 |
| WO | 95/24394 | 9/1995 |
| WO | 96/05165 | 2/1996 |
| WO | 96/19458 | 6/1996 |
| WO | 96/20913 | 7/1996 |
| WO | 97/00876 | 1/1997 |
| WO | 97/12853 | 4/1997 |
| WO | 97/49709 | 12/1997 |
| WO | 9749709 | * 12/1997 |
| WO | 99/43708 | 9/1999 |
| WO | 99/58486 | 11/1999 |
| WO | 00/53562 | 9/2000 |
| WO | 00/66680 | 11/2000 |

OTHER PUBLICATIONS

Allegretto, et al., "Retinoid X Receptor Acts as a Hormone Receptor in Vivo to Induce a Key Metabolic Enzyme for 1,25–Dihydroxyvitamin $D_3$," *J. of Biol. Chem* 270:23906 (1995).

Allegretto, et al., "Transactivation Properties of Retinoic Acid and Retinoid X Receptors in Mammalian Cells and Yeast," J. Biol. Chem., 268(35):26625–26633 (1993).

Apfel, et al., "A retinoic acid receptor α antagonist selectively counteracts retinoic acid effects," *Proc. Natl. Acad. Sci.* 89:7129 (1992).

Atarashi, et al., "Asymmetric Reduction of 7,8–Difluoro–3–methyl–2H–1,4–benzoxazine. Synthesis of a Key Intermediate of (S)–(+)–Ofloxacin (DR–3355)," *J. Heterocyclic Chem.* 28:329–31 (1991).

Atkins, R.L. et al., "Substituted Coumarins and Azacoumarins. Synthesis and Flourescent Properties," *J. Org. Chem.*, 43(10):1975–1980 (1978).

(List continued on next page.)

*Primary Examiner*—Alan L. Rotman
*Assistant Examiner*—Binta Robinson
(74) *Attorney, Agent, or Firm*—Paul, Hastings, Janofsky & Walker LLP

(57) ABSTRACT

Non-steroidal compounds and compositions which are agonists, partial agonists, and antagonists for androgen receptors and methods of preparation for the non-steroidal compounds and compositions.

19 Claims, No Drawings

U.S. PATENT DOCUMENTS

| | | | |
|---|---|---|---|
| 5,198,567 A | 3/1993 | Lang et al. | 560/56 |
| 5,320,833 A | 6/1994 | Deckers et al. | 424/59 |
| 5,391,569 A | 2/1995 | Brion et al. | 514/456 |
| 5,391,766 A | 2/1995 | Klaus et al. | 549/23 |
| 5,688,808 A | 11/1997 | Jones et al. | 514/285 |
| 5,688,810 A | 11/1997 | Jones et al. | 514/311 |
| 5,693,646 A | 12/1997 | Jones et al. | 514/285 |
| 5,693,647 A | 12/1997 | Jones et al. | 514/285 |
| 5,696,127 A | 12/1997 | Jones et al. | 514/285 |
| 5,696,130 A | 12/1997 | Jones et al. | 514/291 |
| 5,705,167 A | 1/1998 | Bernardon et al. | 424/401 |
| 5,721,103 A | 2/1998 | Boehm et al. | 435/7.1 |
| 5,776,699 A | 7/1998 | Klein et al. | 435/7.2 |
| 5,910,508 A | 6/1999 | Thoreau et al. | 514/432 |
| 5,968,908 A | 10/1999 | Epstein et al. | 514/42 |
| 5,977,108 A | 11/1999 | Kikuchi et al. | 303/192 |
| 5,977,125 A | 11/1999 | Hibi et al. | 514/277 |
| 6,030,964 A | 2/2000 | Hibi et al. | 514/183 |
| 6,133,309 A | 10/2000 | Bollag et al. | 514/432 |
| 6,147,224 A | 11/2000 | Vuligonda et al. | 548/518 |

OTHER PUBLICATIONS

Aurell, et al., "Trienediolates of Hexadienoic Acids in Synthesis, Synthesis of Retinoic and not Retinoic Acids." *Tetrahedron* 49:6089 (1993).

Barluenga, et al., "A New Method for the Synthesis of Pyridines," *Synthesis* 191 (1975).

Beard, et al., "Synthesis and Structure–Activity Relationships of Stilbene Retinoid Analogs Substituted with Heteroaromatic Carboxylic Acids," *J. Med. Chem.* 38:2820 (1995).

Berger et al., "Interaction of Glucocorticoid Analogues With The Human Glucocorticoid Receptor," *J. Steroid. Biochem. Molec. Biol.* 41(3–8):733–738 (1992).

Bestmann, et al., "Cumulated Yields as Building Blocks for the Synthesis of Heterocycles," *Angew. Chem. Int. Ed. Engl.* 15(2):115–116 (1976).

Bissell, E.R. et al., "Synthesis and Chemistry of 7–Amino–4–(trifluormethyl)coumarin and Its Amino Acid and Peptide Derivatives," *J. Org. Chem.*, 45:2283–7 (1980).

Bissonnette, et al., "9–cis Retinoic Acid Inhibition of Activation–Induced Apoptosis Is Mediated via Regulation of Fas Ligand and Requires Retinoic Acid Receptor and Retinoid X Receptor Activation," *Mol. Cell. Biol.* 15:5576–5585 (1995).

Biswas, et al., "Montmorillonite clay as condensing agent in Pechmann reaction for the synthesis of courmarin derivatives," *Indian J. Chem.* 31B:628 (1992).

Blatt, The Fries Reaction Chapter 11 *Org. React.* 1:342 (1942).

Boehm, et al. "Synthesis and Structure–Activity Relationships of Novel Retinoid X Receptor Selective Retinoids," *J. Med. Chem.* 37:2930 (1994).

Boehm, et al., "Design and Synthesis of Potent Retinoid X Receptor Selective Ligands That Induce Apoptosis in Leukemia Cells," *J. Med. Chem.* 38:3146 (1995).

Boehm, et al., "Synthesis of High Specific activity [3H]–9–Cis Retinoic Acid and its Application for Identifying Retinoids with Unusual Binding Properties," *J. Med. Chem.*, 37:408 (1994).

Canan–Koch, et al., "Identification of the First Retinoid X Receptor Homodime Antagonist," *J. Med. Chem.* 39(17):3229 (1996).

Catellani, et al., "A New Palladium–catalyzed Synthesis of 3,4–Disubstituted Coumarins from 3–Alkenoates of ortho–Iodophenol, Phenylacetylene and Carbon Monoxide," *Tetrahedron Lett.* 35(32):5923 (1994).

Chapelo, et al., "Heteroaromatoc Analogues of the $\alpha_2$–Adrenoreceptor Partial Agonist Clonidine," *J. Med. Chem.*, 32:1627–1630 (1989).

Chemistry and Biology of Synthetic Retinoids, Dawson and Okamuna, Eds., CRC Press, Florida: Chapters 3,8,14, and 16 (1990).

Clark and Miller, "Hydrogen Bonding in Organic Synthesis V: Potassium Fluoride in Carboxylic Acids as an Alternative To Crown Ether With Acids Salts in The Preparation of Phenacyl Esters," *Tetrahedron Lett.* 7:599 (1977).

Dawson and Hobbs, "Ch. 2—The Synthetic Chemistry of Retinoids," in *The Retinoids: Biology, Chemistry and Medicine*, 2nd edition, edited by Sporn et al., Raven Press, New York, pp. 5–178 (1994).

Dawson, et al., "Effects of Structural Modification in the C7–C11 Region of the Retinoid Skeleton on Biological Activity in a Series of Aromatic Retinoids," *J. Med. Chem.* 32:1504 (1989).

Edwards, et al., "5–Ayrl–1, 2–dihydro–5H–Chromeno[3, 4–ʃ]quinolines as Potent, Orally Active, Nonsteroidal Progesterone Receptor Agonists: The Effect of D–Ring Substituents," J. Med. Chem., 41:303–331 (1998).

Edwards, et al., "New Nonsteroidal Androgen Receptor Modulators Based on 4–(Trifluormethyl)–2–(1H)–Pyrrolidino[3,2–g]Quinolinone," *Bioorg. Med. Chem. Lett.* 8:745–750 (1998).

Edwards, J.P., et al., "Preparation, Resolution, and Biological Evaluation of 5–Aryl–1,2–dihydro–5H–chromeno[3, 4–ʃ]quinolines: Potent, Orally Active, Nonsteroidal Progesterone Receptor Agonists," *J. Med. Chem.*, 41(15):2779–85 (1998).

Evans, R.M., "The Steroid and Thyroid Hormone Receptor Superfamily," *Science* 240:889–895 (1988).

Eyrolles, et al., "Retinobenzoic Acids. 6. Retinoid Antagonists with a Heterocyclic Ring," *J. Med. Chem* 37:1508 (1994).

Eyrolles, et al., "Retinoid Antagonists: Molecular Design Based on the Ligand Superfamily in Concept," *Med. Chem. Res.*, 2:361–367 (1992).

Forman, et al., "Unique Response Pathways Are Established by Allosteric Interactions among Nuclear Hormone Receptors," *Cell* 81:541–550 (1995).

Fries and Fink, "Uber Homologe des Cumaranons und ihre Abkommlinge," *Ber.* 41:4271 (1908).

Fries and Pfaffendorf, "Uber ein Kondensationsprodukt des Cumaranons und seine Umwandlung in Oxindirubin," *Ber.* 43:212 (1910).

Giguere, et al., "Identification of a receptor for the morphogen retinoic acid," *Nature* 330:624–629 (1987).

Goralski, et al., "Boranes in Synthesis. 3. Conversion of the Morpholine and Pyrrolidine Enamines of Symmetrical Dialkylketones to the Correspondng threo–β–Amino Alcohols via Hydroboration/Oxidation," *Tetrahedron Lett.* 35(20):3251–54 (1994).

Gromova, G.N. et al., *Khim Prom St.*, 43(2):97–8 (1967).

Hamann, L.G. et al., "Synthesis and biological activity of a novel series of nonsteroidal, peripherally selective androgen receptor antagonists derived from 1,2–dihydropyridono 5, 6–g!quinolines," *J. Med. Chem.*, 41(4):623–39 (1998).

Hamann, L.G., et al., "Discovery of a Potent, Oraly Active, Nonsteroidal Androgen Receptor Agonist: 4–Ethyl–1,2,3, 4–tetrahydro–6–(trifluoromethyl)–8–pyridono[5,6–g]–quinoline," *J. Med. Chem.*, 42(2):210–12 (1999).

Hershberger, et al., "Myotrophic Activity of 19–Nortestosterone and Other Steroids Determined by Modified Levator Anti Muscle Method" *Proc. Soc. Exptl. Biol. Med.* 83:175–178 (1953).

Heyman et al., "9–Cis Retenoic Acid is a High Affinity Ligand for the Retinoid X Receptor," *Cell* 68:397–406 (1992).

Hollenberg and Evans, "Multiple and Cooperative Trans–Activation Domains of the Human Glucocorticoid Receptor," *Cell* 55:899–906 (1988).

Ishikawa et al., "A Functional Retinoic Acids Receptor Encoded by the Gene on Human Chromosome 12," *Molecular Endocrinology* 4(6):837–844 (1990).

Ivanov, et al., Chem Abstracts No. 95:97624, "Synthesis and properties of derivatives of 2,2,4–trimethyl substituted quinolines and some of their analogs," *Izv. Akad. Nauk. SSSR Ser. Khim.*, 3:628–633 (1981).

Jones, "The Structure, Reactions, Synthesis and Uses of Heterocyclic Compounds," *Comprehensive Heterocyclic Chemistry* vol. 2, Chap. 2.08, 421–426 (1984).

Jow, et al., "The Human Peroxisome Proliferator–activated Receptor (PPAR) Subtype NUC1 Prepresses the Activation of hPPARα and Thyroid Hormone Receptors," *J. Biol. Chem*, 270(8):3836–3840 (1995).

Kagechika, et al., "Retinobenzoic Acids. 2. Structure–Activity Relationship of Chalone–4–carboxylic Acids and Glavone'–carboxlic Acids," *J. Med. Chem.*, 32(4):834 (1989).

Kagechika, et al., "Retinobenzoic Acids. 3. Structure–Activity Relationships of Retinoidal Azobenzene–4–carboxylic Acids and Stilbene–4–carboxylic Acids," *J. Med. Chem.* 32(5):1098 (1989).

Kagechika, et al., "Retinobenzoic Acids. 4. Conformation of Aromatic Amides with Retinoidal Activity. Importance of trans–Amide Structure for the Activity," *J. Med. Chem.* 32(10):2292 (1989).

Kaneko, et al., "Retinoid Antagonists," *Med. Chem. Res.*, 1:220–225 (1991).

Keidel, et al., "Different Agonist–and Antagonist–Induced Conformational Changes in Retinoic Acid Receptors Analyzed by Protease Mapping," *Mol. Cell. Biol.* 14(1):287 (1994).

Kliewer et al., "Convergence of 9–cis retinoic acid and peroxisome proliferator signalling pathways through heterodimer formation of their receptors," *Nature* 358:771–774 (1992).

Kong, et al., "Effects of isosteric pyridone replacements in androgen antagonists based on 1,2–dihydro–and 1,2,3,4–tetrahydro–2,2–dimethyl–6–trifluoromethyl–8–pyridono 5,6–g quinolines" *Bioorg. Med. Chem. Lett.* 10(5), 411–414 (2000).

Kurokawa, et al., "Regulation of retinoid signalling by receptor polarity and allosteric control of ligand binding," *Nature*, 371:528–531 (1994).

Labrie, et al., "Science behind total androgen blockade: from gene to combination therapy," *Clin. Invest. Med.* 16(6):475–492 (1993).

Lee, et al., "A synthetic retinoid antagonist inhibits the human immunodeficiency virus type 1 promoter," *Proc. Natl. Acad. Sci.* 91:5632 (1994).

Levin, et al., "9–Cis retinoic acid stereoisomer binds and activates the nuclear receptor RXRα," *Nature*, 355:359–361 (1992).

Ley et al., "Tetrapropylammonium Perruthenate, $Pr_4N^+$ $RuO^-_4$, TPAP: A Catalytic Oxidant for Organic Synthesis," *Synthesis* 639 (1994).

Li, et al., "Montmorillonite Clay Catalysts. Part 7. An Environmentaly Friendly Procedure for the Synthesis of Coumarins via Pechmann Condensation of Phenols with Ethyl Acetoacetate," *J. Chem. Res.* 38–39 (1998).

Liu and Asato, "Photochemistry and Synthesis of Stereoisomers of Vitamin A," *Tetrahedron* 40(11):1931–1969 (1984).

Loeliger, et al., "Arotinoids, a new class of highly active retinoids," *Eur. J. Med. Chem* 15:9 (1980).

Luke, et al., "The Male Sex Accessory Tissues; Structure, Androgen Action, and Physiology," *The Physiology of Reproduction*, 1435–1487 (1994).

Mangelsdorf et al., "A Direct Repeat in the Cellular Retinol–Binding Protein Type II Gene Confers Differential Regulation by RXR and RAR," *Cell* 66:555–561 (1991).

Mangelsdorf et al., "Ch. 8—The Retinoid Receptors," in *The Retinoids: Biology, Chemistry and Medicine*, 2nd edition, Sporn ed., Raven Press Ltd., New York, pp. 319–349 (1994).

Mangelsdorf et al., "Nuclear receptor that identifies a novel retinoic acid response pathway," *Nature* 345:224–229 (1990).

Maryanoff and Reitz,, "The Wittig Olefination Reaction and Modifications Involving Phosphoryl–Stabalized Carbanions. Stereochemistry, Mechanism, and Sepected Synthetic Aspects," *Chem. Rev.* 89(4):863–927 (1989).

Matsumoto, et al., "Novel Potassium Channel Activators: Synthesis and Structure–Activity Relationship Studies of 3,4–Dihydro–2H–1,4–benzoxazine Derivatives," *Chem. Pharm. Bull.*, 44(1):103–114 (1996).

McDonnell, et al., "Analysis of Estrogen Receptor Function in Vitro Reveals Three Distinct Classes of Antiestrogens," *Mol. Endo.* 9(6):659–669 (1995).

Mitscher, et al., "Chiral DNA Gyrase Inhibitors. 2. Asymmetric Synthesis and Biological Activity of the Enantiomers of 9–Fluoro–3–methyl–10–(4–methyl–1–piperazinyl)–7–oxo–2,3–dihydro–7H–pyrido[1,2,3–de]–1, 4–benzoxazine–6–carboxylic Acid (Ofloxacin)," *J. Med. Chem.* 30(12):2283 (1987).

Mukherjee et al., "Human and Rat Peroxisome Proliferator Activated Receptors (PPARs) Demonstrate Similar Tissue Distribution but Different Responsiveness to PPAR Activators," *J. Steroid Biochem. Molec. Biol.* 51(3–4):157–166 (1994).

Mukherjee, et al., "Identification, characterization, and Tissue Distribution of Human Peroxisome Proliferator–activated Receptor (PPAR) Isoforms PPARγ2 versus PPARγ1 and Activation with Retinoid X Receptor Agonists and Antagonists," *Journ. Biol. Chem.* 272(12):8071–8076 (1997).

Munk, et al., "Synthesis and Evaluation of 2–[(5–Methylbenz–1–ox–4–azin–6–yl) imino]imidazoline, a Potent, Peripherally Acting $α_2$ Adrenoreceptor Agonist,"*J. Med. Chem.*, 39(18):3533–3538 (1996).

Okuda, et al., "Testosterone Dependent Regulation of the Enzymes Involved in DNA Synthesis in the Rat Ventral Prostate," *J. Urol.* 145:188–191 (1991).

Patent Abstracts of Japan, vol. 4, No. 019, Feb. 16, 1980; JP 54 154797.

Patent Abstracts of Japan, vol. 9, No. 188, Aug. 3, 1985; JP 60 056985.

Patent Abstracts of Japan, vol. 1999, No. 14, Dec. 22, 1999; JP 11 242304.

Petkovich et al., "A human retinoic acid receptor which belongs to the family of nuclear receptors," *Nature* 330:444–450 (1987).

Pine, et al., "Carbonyl Methylenation Using a Titanium–Aluminum (Tebbe) Complex," *J. Org. Chem.* 50(8):1212–1216 (1985).

Quast, et al., "Synthesis and reactions of some pyrido 3,2-g!quinolines (1,8-diazaanthracenes)," *Liebigs Ann. Chem.*, 133–46 (1984).

Rodbard, D. "Mathematics and statistics of ligand assays: an illustrated guide" In: J. Langon and J.J. Clapp, eds., Ligand Assay, Masson Publishing U.S.A, Inc., New York, pp. 45–99, (1981).

Roy, et al., "Synergistic Activation of Retinoic Acid (RA)–Responsive Genes and Induction of Embryonal Carcinoma Cell Differentiation by an RA Receptor α (RARα)–, RARβ–, or RARγ–Selective Ligand in Combination with a Retinoid X Receptor–Specific Ligand," *Mol. Cell. Biol.* 15(12):6481–6487 (1995).

Sala, et al., "Depsidone Synthesis. Part 14. The Total Synthesis of Psoromic Acid: Isopropyl Ethers as Useful Phenolic Protective Groups," *J. Chem. Soc. Perkin. Trans.* I:2593 (1979).

Sato and Otera, "CsF in Organic Synthesis. A Practical Method for Inversion of Secondary Mesylates," *Syn. Lett.* 336(1995).

Sato, et al., "CsF in Organic Synthesis: Tuning of N–or O–Alkylation of 2–Pyridone," *Synlett* 845–846 (1995).

Sethna and Phadke, The Pechmann Reaction *Organic Reactions* 7:1–58 (1953).

Sherman, et al., "Central Hypothyroidism Associated with Retinoid X Receptor–Selective Ligands," *N. Engl. J. Med.* 340(14):1075–1079 (1999).

Shridhar, et al., "A General and Convenient Synthesis of 2H–1,4–Benzoxazin–3(4H)–ones," *Org. Prep. Proc. Int.* 14(3):195 (1982).

Simental, et al., "Transcriptional activation and nuclear targeting signals of the human androgen receptor," *J. Biol. Chem.* 266(1):510–518 (1991).

Strickland et al., "Structure–Activity Relationships of a New Series of Retinoidal Benzoic Acid Derivatives as Measured by Induction of Differentiation of Murine F9 Teratocarcinoma Cells and Human HL–60 Promyelocytic Leukemia Cells," *Cancer Research* 43:5268–5272 (1983).

Tegley, C.M., et al., "5–Benzylidene 1,2–Dihydrochromeno [3,4–f]quinolines, A Novel Class of Nonsteroidal Human Progesterone Receptor Agonists," *J. Med. Chem.*, 41(22):4354–9 (1998).

Trost and Toste, "A New Palladium–Catalyzed Addition: A Mild Method for the Synthesis of Coumarins," *J. Am. Chem. Soc.* 118(26):6305 (1996).

Tzukerman et al., "Human estrogen receptor transactivational capacity is determined by both cellular and promoter context and mediated by two functionally distinct intramolecular regions," *Molecular Endocrinology* 8:21–30 (1994).

Umesono, et al., "Retinoic acid and thyroid hormone induce gene expression through a common responsive element," *Nature* 336:262 (1988).

Voss, "2,4–Bis(4–methoxyphenyl)–1,3,2,4–dithiadiphosphetane 2,4–Disulfide," *Encyclopedia of Reagents for Organic Synthesis*, 1:530–533 (1995).

Wagaw, et al., "Palladium–Catalyzed Coupling of Optically Active Amines with Aryl Bromides," *J. Am. Chem. Soc.* 119:8451–8458 (1997).

Walsh, et al., "Inhibition of extratesticular stimuli to prostatic growth in the castrated rat by antianrogens," *Endocrinology* 86:624 (1970).

Xie, et al., *Chinese Chemical Letters* 6:857 (1995).

Yoshimura, et al. "A Novel Type of Retinoic Acid Receptor Antagonist: Synthesis and Structure–Activity Relationships of Heterocyclic Ring Containing Benzoic Acid Derivatives," *J. Med. Chem.* 38(16):3163 (1995).

Zhi, et al., "5–Aryl–1,2–dihydrochromeno [3,4–f]quinolines: A Novel Class of Nonsteroidal Human Progesterone Receptor Agonists," *J. Med Chem.*, 41(3):291–302 (1998).

\* cited by examiner

8-SUBSTITUTED-6-TRIFLOUROMETHYL-9-PYRIDO [3,2-G] QUINOLINE COMPOUNDS AS ANDROGEN RECEPTOR MODULATORS

This application claims priority to U. S. Provisional Application Ser. No. 60/151,235, filed Aug. 27, 1999, the entire disclosure of which is hereby incorporated by reference.

FIELD OF THE INVENTION

This invention relates to non-steroidal compounds that are modulators (i.e. agonists and antagonists) of androgen receptors, and to methods for the making and use of such compounds.

BACKGROUND OF THE INVENTION

Intracellular receptors (IRs) form a class of structurally-related genetic regulators scientists have named "ligand dependent transcription factors." R. M. Evans, *Science*, 240:889 (1988). Steroid receptors are a recognized subset of the IRs, including the progesterone receptor (PR), androgen receptor (AR), estrogen receptor (ER), glucocorticoid receptor (GR) and mineralocorticoid receptor (MR). Regulation of a gene by such factors requires both the IR itself and a corresponding ligand which has the ability to selectively bind to the IR in a way that affects gene transcription.

Ligands to the IRs can include low molecular weight native molecules, such as the hormones progesterone, estrogen and testosterone, as well as synthetic derivative compounds such as methoxyprogesterone acetate, diethylstilbesterol and 19-nortestosterone. These ligands, when present in the fluid surrounding a cell, pass through the outer cell membrane by passive diffusion and bind to specific IR proteins to create a ligand/receptor complex. This complex then translocates to the cell's nucleus, where it binds to a specific gene or genes present in the cell's DNA. Once bound to this regard, a compound which binds an IR and mimics the effect of the native ligand is referred to as an "agonist", while a compound that inhibits the effect of the native ligand is called an "antagonist."

Ligands to the steroid receptors are known to play an important role in health of both women and men. For example, the native female ligand, progesterone, as well as synthetic analogues, such as norgestrel (18-homonorethisterone) and norethisterone (17α-ethinyl-19-nortestosterone), are used in birth control formulations, typically in combination with the female hormone estrogen or synthetic estrogen analogues, as effective modulators of both PR and ER. On the other hand, antagonists to PR are potentially useful in treating chronic disorders, such as certain hormone dependent cancers of the breast, ovaries, and uterus, and in treating non-malignant conditions such as uterine fibroids and endometriosis, a leading cause of infertility in women. Similarly, AR antagonists, such as cyproterone acetate and flutamide have proved useful in the treatment of prostatic hyperplasia and cancer of the prostate.

The effectiveness of known modulators of steroid receptors is often tempered by their undesired side-effect profile, particularly during long-term administration. For example, the effectiveness of progesterone and estrogen agonists, such as norgestrel and diethylstilbesterol respectively, as female birth control agents must be weighed against the increased risk of breast cancer and heart disease to women taking such agents. Similarly, the progesterone antagonist, mifepristone (RU486), if administered for chronic indications, such as uterine fibroids, endometriosis and certain hormone-dependent cancers, could lead to homeostatic imbalances in a patient due to its inherent cross-reactivity as a GR antagonist. Accordingly, identification of compounds which have good specificity for one or more steroid receptors, but which have reduced or no cross-reactivity for other steroid or intracellular receptors, would be of significant value in the treatment of male and female hormone responsive diseases.

A group of quinoline analogs having an adjacent polynucleic ring system of the indene or fluorene series or an adjacent polynucleic heterocyclic ring system with substituents having a nonionic character have been described as photoconductive reducing agents, stabilizers, laser dyes and antioxidants. See e.g., U.S. Pat. Nos. 3,798,031; 3,830,647; 3,832,171; 3,928,686; 3,979,394; 4,943,502 and 5,147,844 as well as Soviet Patent No. 555,119; R. L. Atkins et al., *J. Org. Chem.*, 43:1975 (1978), E. R. Bissell et al., *J. Org. Chem.*, 45:2283 (1980), and G. N. Gromova et al., *Khim. Prom-st.*, 43:97 (Moscow, 1967). Further, a group of quinoline derivatives was recently described as modulators of steroid receptors. See, e.g., WO 96/19458, published Jun. 27, 1996. A recent paper describes the synthesis and biological activity of the pyridone-containing precursors to the present series of molecules. See, e.g., L. G. Hamann, et al., *J. Med. Chem.*, 41:623 (1998).

SUMMARY OF THE INVENTION

The present invention is directed to compounds, pharmaceutical compositions, and methods for modulating processes mediated by androgen receptors (AR). More particularly, the invention relates to non-steroidal compounds and compositions which are high affinity, high specificity agonists, partial agonists (i.e., partial activators and/or tissue-specific activators) and antagonists for androgen receptors. Also provided are methods of making such compounds and pharmaceutical compositions, as well as critical intermediates used in their synthesis.

These and various other advantages and features of novelty which characterize the invention are pointed out with particularity in the claims annexed hereto and forming a part hereof. However, for a better understanding of the invention, its advantages, and objects obtained for its use, reference should be made to the accompanying drawings and descriptive matter, in which there is illustrated and described preferred embodiments of the invention.

DETAILED DESCRIPTION OF PREFERRED EMBODIMENTS

As used herein, the following terms are defined with the following meanings, unless explicitly stated otherwise. Furthermore, in an effort to maintain consistency in the naming of compounds of similar structure but differing substituents, the compounds described herein are named according to the following general guidelines. The numbering system for the location of substituents on such compounds is also provided.

The term "alkyl" refers to an optionally substituted straight-chain or branched-chain hydrocarbon radical having from 1 to about 10 carbon atoms, more preferably from 1 to about 6 carbon atoms, and most preferably from 1 to about 4 carbon atoms. Examples of alkyl radical include methyl, ethyl, n-propyl, isopropyl, n-butyl, isobutyl, sec-butyl, tert-butyl, pentyl, hexyl, octyl and the like.

The term "alkenyl" refers to a straight-chain or branched-chain hydrocarbon radical having one or more carbon-carbon double-bonds and having from 2 to about 10 carbon atoms, preferably from 2 to about 6 carbon atoms, and most preferably from 2 to about 4 carbon atoms. Preferred alkeny groups include allyl. Examples of alkenyl radicals include ethenyl, propenyl, 1,4-butadienyl and the like.

The term "allyl" refers to the radical $H_2C=CH-CH_2$.

The term "alkynyl" refers to a straight-chain or branched-chain hydrocarbon radical having one or more carbon-carbon triple-bonds and having from 2 to about 10 carbon atoms, preferably from 2 to about 6 carbon atoms, and most preferably from 2 to about 4 carbon atoms. Examples of alkynyl radicals include ethynyl, propynyl, butynyl and the like.

The term "aryl" refers to optionally substituted aromatic ring systems. The term aryl includes monocyclic aromatic rings, polycyclic aromatic ring systems, and polyaromatic ring systems. The polyaromatic and polycyclic ring systems may contain from two to four, more preferably two to three, and most preferably two, rings. Preferred aryl groups include 5- or 6-membered aromatic ring systems.

The term "heteroaryl" refers to optionally substituted aromatic ring systems having one or more heteroatoms such as, for example, oxygen, nitrogen and sulfur. The term heteroaryl may include five- or six-membered heterocyclic rings, polycyclic heteroaromatic ring systems, and polyheteroaromatic ring systems where the ring system has from two to four, more preferably two to three, and most preferably two, rings. The terms heterocyclic, polycyclic heteroaromatic, and polyheteroaromatic include ring systems containing optionally substituted heteroaromatic rings having more than one heteroatom as described above (e.g., a six membered ring with two nitrogens), including polyheterocyclic ring systems from two to four, more preferably two to three, and most preferably two, rings. Preferably, heteroaryl groups have from one to The term heteroaryl includes ring systems such as, for example, pyridine, quinoline, furan, thiophene, pyrrole, imidazole and pyrazole.

The term "alkoxy" refers to an alkyl ether radical wherein the term alkyl is defined as above. Examples of alkoxy radicals include methoxy, ethoxy, n-propoxy, isopropoxy, n-butoxy, iso-butoxy, sec-butoxy, tert-butoxy and the like.

The term "aryloxy" refers to an aryl ether radical wherein the term aryl is defined as above. Examples of aryloxy radicals include phenoxy, benzyloxy and the like.

The term "cycloalkyl" refers to a saturated or partially saturated monocyclic, bicyclic or tricyclic alkyl radical wherein each cyclic moiety has about 3 to about 8 carbon atoms. Examples of cycloalkyl radicals include cyclopropyl, cyclobutyl, cyclopentyl, cyclohexyl and the like.

The term "cycloalkylalkyl" refers to an alkyl radical as defined above which is substituted by a cycloalkyl radical having from about 3 to about 8 carbon atoms.

The term "arylalkyl" refers to an alkyl radical as defined above in which one hydrogen atom is replaced by an aryl radical as defined above, such as, for example, benzyl, 2-phenylethyl and the like. Preferably, arylalkyl refers to arylmethyl.

The terms alkyl, alkenyl, and alkynyl include optionally substituted straight-chain, branched-chain, cyclic, saturated and/or unsaturated structures, and combinations thereof.

The terms cycloalkyl, allyl, aryl, arylalkyl, arylalkyl, heteroaryl, alkynyl, and alkenyl include optionally substituted cycloalkyl, allyl, aryl, arylalkyl, arylalkyl, heteroaryl, alkynyl, and alkenyl groups.

The terms haloalkyl, haloalkenyl and haloalkynyl include alkyl, alkenyl and alkynyl structures, as described above, that are substituted with one or more fluorines, chlorines, bromines or iodines, or with combinations thereof.

The terms heteroalkyl, heteroalkenyl and heteroalkynyl include optionally substituted alkyl, alkenyl and alkynyl structures, as described above, in which one or more skeletal atoms are oxygen, nitrogen, sulfur, or combinations thereof.

The substituents of an "optionally substituted" structure include, for example, one or more, preferably 1 to 4, and more preferably 1 to 2 of the following preferred substitutents: alkyl, alkenyl, alkynyl, aryl, heteroaryl, alkoxy, aryloxy, cycloalkyl, cycloalkylalkyl, arylalkyl, amino, alkylamino, dialkylamino, F, Cl, Br, I, $C_1$–$C_6$ alkyl, $OR^2$, $NR^{13}R^{14}$ and $SR^2$.

An 8-pyridono[5,6-g]quinoline is represented by the following structure.

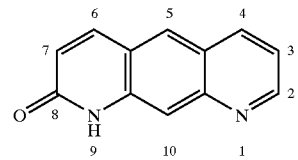

An 9-pyrido[3,2-g]quinoline is represented by the following structure.

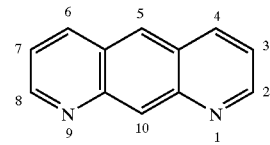

Compounds of the present invention are represented as those having the formula:

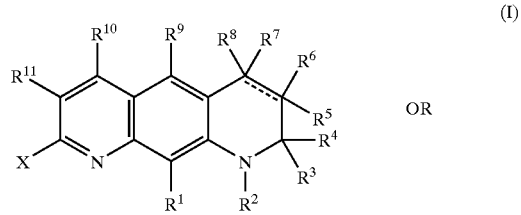

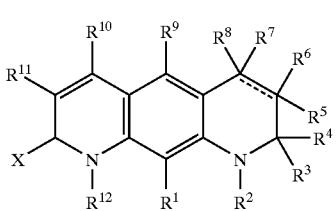

(II)

wherein:
- $R^1$ is hydrogen, $C_1$–$C_6$ alkyl, F, Cl, Br, I, $NO_2$, $OR^2$, $NR^{13}R^{14}$, or $SR^2$;
- $R^2$ is hydrogen, $C_1$–$C_6$ alkyl or $C_1$–$C_6$ alkenyl, wherein the $C_1$–$C_6$ alkyl and $C_1$–$C_6$ alkenyl are optionally substituted with $C_1$–$C_6$ alkyl, arylalkyl or heteroaryl;
- $R^3$ and $R^4$ each independently represent hydrogen, $C_1$–$C_6$ alkyl, $C_1$–$C_6$ haloalkyl, $C_1$–$C_6$ perhaloalkyl, $C_1$–$C_6$ alkenyl, $C_1$–$C_6$ alkynyl, aryl, or heteroaryl, wherein the alkyl, haloalkyl, perhaloalkyl, alkenyl, alkynyl, aryl, and heteroaryl are optionally substituted with hydrogen, F, Cl, Br, $C_1$–$C_4$ alkyl, $OR^2$, $NR^{13}R^{14}$, or $SR^2$; or optionally,
- $R^3$ and $R^4$ may be taken together form a three- to seven-membered ring optionally substituted with hydrogen, F, Cl, Br, $C_1$–$C_4$ alkyl, $OR^2$, $NR^{13}R^{14}$, or $SR^2$;
- $R^5$ and $R^6$ each independently represent hydrogen, $C_1$–$C_6$ alkyl, $C_1$–$C_6$ haloalkyl, $C_1$–$C_6$ perhaloalkyl, $C_1$–$C_6$ alkenyl, $C_1$–$C_6$ alkynyl, aryl, or heteroaryl, wherein the alkyl, haloalkyl, perhaloalkyl, alkenyl, alkynyl, aryl, and heteroaryl are optionally substituted with hydrogen, F, Cl, Br, $C_1$–$C_4$ alkyl, $OR^2$, $NR^{13}R^{14}$, or $SR^2$; or optionally,
- $R^5$ and $R^6$ may be taken together form a carbonyl, an imine, or a three- to seven-membered ring optionally substituted with hydrogen, F, Cl, Br, $C_1$–$C_4$ alkyl, $OR^2$, $NR^{13}R^{14}$, or $SR^2$;
- $R^7$ and $R^8$ each independently represent hydrogen, $C_1$–$C_6$ alkyl, $C_1$–$C_6$ haloalkyl, $C_1$–$C_6$ perhaloalkyl, $C_1$–$C_6$ alkenyl, $C_1$–$C_6$ alkynyl, aryl, or heteroaryl, wherein the alkyl, haloalkyl, perhaloalkyl, alkenyl, alkynyl, aryl, and heteroaryl are optionally substituted with hydrogen, F, Cl, Br, $C_1$–$C_4$ alkyl, $OR^2$, $NR^{13}R^{14}$, or $SR^2$; or optionally,
- $R^7$ and $R^8$ may be taken together form a carbonyl, an imine, or a three- to seven-membered ring optionally substituted with hydrogen, F, Cl, Br, $C_1$–$C_4$ alkyl, $OR^2$, $NR^{13}R^{14}$, or $SR^2$;
- $R^9$ represents hydrogen, $C_1$–$C_4$ alkyl, F, Cl, Br, I, $OR^2$, $NR13R14$, or $SR^2$;
- $R^{10}$ is represents hydrogen, F, Cl, Br, $CF_3$, $CF_2OR^2$, $CH_2OR^2$, $OR^2$, $C_1$–$C_6$ alkyl, $C_1$–$C_6$ haloalkyl, $C_1$–$C_6$ perhaloalkyl, aryl, or heteroaryl, wherein the alkyl, haloalkyl, perhaloalkyl, aryl, and heteroaryl are optionally substituted with hydrogen, F, Cl, Br, $C_1$–$C_4$ alkyl, $OR^2$, $NR^{13}R^{14}$, or $SR^2$;
- $R^{11}$ represents hydrogen, F, Cl, Br, I, $C_1$–$C_6$ alkyl, $C_1$–$C_6$ perhaloalkyl, $C_1$–$C_6$ perhaloalkyl, $C_1$–$C_6$ alkenyl, $C_1$–$C_6$ alkynyl, aryl, and heteroaryl, wherein the alkyl, haloalkyl, perhaloalkyl, alkenyl, alkynyl, aryl, or heteroaryl are optionally substituted with hydrogen, F, Cl, Br, $C_1$–$C_4$ alkyl, $OR^2$, $NR^{13}R^{14}$, or $SR^2$;
- $R^{12}$ represents hydrogen, $C(O)R^{11}$, $SR^2$, $S(O)R^{13}$, $S(O_2)R^{13}$, $C_1$–$C_6$ alkyl, $C_1$–$C_6$ alkenyl, aryl, arylalkyl or heteroaryl, wherein the alkyl, alkenyl, aryl, arylalkyl and heteroaryl are optionally substituted with hydrogen, F, Cl, Br, $C_1$–$C_4$ alkyl, $OR^2$, $N^{13}R^{14}$, or $SR^2$;
- X represents hydrogen, F, Cl, Br, I, CN, $CF_3$, $SR^2$, $S(O)R^{13}$, $SO_2R^{13}$, $SO_3R^{13}$, $NR^{13}R^{14}$, $CF_3$, $NO_2$, or $R^{13}$;
- $R^{13}$ and $R^{14}$ each independently represents hydrogen, $C(O)R^{11}$, $SO_2R^3$, $C_1$–$C_6$ alkyl, $C_1$–$C_6$ alkenyl, $C_1$–$C_6$ haloalkyl, $C_1$–$C_6$ perhaloalkyl, aryl, arylalkyl or heteroaryl, wherein the alkyl, alkenyl, haloalkyl, perhaloalkyl, aryl, arylalkyl, and heteroaryl are optionally substituted with hydrogen, F, Cl, Br, $C_1$–$C_4$ alkyl, $OR^2$, $NR^{13}R^{14}$, or $SR^2$;
- with the proviso that when the dotted line in the ring structure is a double bond, $R^6$ and $R^7$ are null;
- and pharmaceutically acceptable salts thereof.

Preferred $R^1$ groups include hydrogen, $C_1$–$C_6$ alkyl, F, Cl, Br, I, $NO_2$, $OR^2$, $NR13R14$, and $SR^2$. More preferred $R^1$ groups include hydrogen and $C_1$–$C_4$ alkyl Most preferably $R^1$ is hydrogen.

Preferred $R^2$ groups include hydrogen, $C_1$–$C_6$ alkyl or $C_1$–$C_6$ alkenyl, wherein the $C_1$–$C_6$ alkyl and $C_1$–$C_6$ alkenyl are preferably substituted with $C_1$–$C_6$ alkyl, arylalkyl or heteroaryl. More preferred $R^2$ groups include hydrogen and $C_1$–$C_4$ alkyl. Most preferably $R^2$ is hydrogen.

Preferred $R^3$ groups include hydrogen, $C_1$–$C_6$ alkyl, $C_1$–$C_6$ perhaloalkyl, $C_1$–$C_6$ alkenyl, $C_1$–$C_6$ alkynyl, aryl, and heteroaryl, wherein the alkyl, perhaloalkyl, alkenyl, alkynyl, aryl, and heteroaryl may be optionally substituted. More preferred $R^3$ groups include hydrogen, $C_1$–$C_6$ alkyl, $C_1$–$C_6$ perhaloalkyl, $C_1$–$C_6$ alkenyl, $C_1$–$C_6$ alkynyl, and $C_1$–$C_6$ allyl. Most preferably, $R^3$ is hydrogen or $C_1$–$C_6$ alkyl.

Also preferred are compounds where $R^3$ is taken with $R^4$ to form a three- to seven-membered ring that is optionally substituted.

Preferred $R^4$ groups include hydrogen, $C_1$–$C_6$ alkyl, $C_1$–$C_6$ perhaloalkyl, $C_1$–$C_6$ alkenyl, $C_1$–$C_6$ alkynyl, aryl, and heteroaryl, wherein the alkyl, perhaloalkyl, alkenyl, alkynyl, aryl, and heteroaryl are optionally substituted. More preferred $R^4$ groups include hydrogen, $C_1$–$C_6$ alkyl, $C_1$–$C_6$ perhaloalkyl, $C_1$–$C_6$ alkenyl, $C_1$–$C_6$ alkynyl, and $C_1$–$C_6$ allyl. Most preferably, $R^4$ is hydrogen or $C_1$–$C_6$ alkyl.

Preferred $R^5$ groups include hydrogen, $C_1$–$C_6$ alkyl, $C_1$–$C_6$ perhaloalkyl, $C_1$–$C_6$ alkenyl, $C_1$–$C_6$ alkynyl, aryl, and heteroaryl, wherein the alkyl, perhaloalkyl, alkenyl, alkynyl, aryl, and heteroaryl are optionally substituted. More preferred $R^5$ groups include hydrogen, $C_1$–$C_6$ alkyl, $C_1$–$C_6$ perhaloalkyl, $C_1$–$C_6$ alkenyl, $C_1$–$C_6$ alkynyl, and $C_1$–$C_6$ allyl. Most preferably, $R^5$ is hydrogen or $C_1$–$C_6$ alkyl.

Also preferred are compounds where $R^5$ is taken with $R^6$ to form a carbonyl, an imine, or a three- to seven-membered ring that is optionally substituted.

Preferred $R^6$ groups include hydrogen, $C_1$–$C_6$ alkyl, $C_1$–$C_6$ perhaloalkyl, $C_1$–$C_6$ alkenyl, $C_1$–$C_6$ alkynyl, aryl, and heteroaryl, wherein the alkyl, perhaloalkyl, alkenyl, alkynyl, aryl, and heteroaryl are optionally substituted. More preferred $R^6$ groups include hydrogen, $C_1$–$C_6$ alkyl, $C_1$–$C_6$ perhaloalkyl and null. Most preferably, $R^6$ is hydrogen.

Preferred $R^7$ groups include hydrogen, $C_1$–$C_6$ alkyl, $C_1$–$C_6$ perhaloalkyl, $C_1$–$C_6$ alkenyl, $C_1$–$C_6$ alkynyl, aryl, and heteroaryl, wherein the alkyl, perhaloalkyl, alkenyl, alkynyl, aryl, and heteroaryl are optionally substituted. Also preferred are compounds where $R^7$ is taken with $R^8$ to form a carbonyl, an imine, or a three- to seven-membered ring that is optionally substituted. More preferred $R^7$ groups include hydrogen, $C_1$–$C_6$ alkyl, $C_1$–$C_6$ perhaloalkyl and null. Most preferably $R^7$ is hydrogen.

Preferred $R^8$ groups include hydrogen, $C_1$–$C_6$ alkyl, $C_1$–$C_6$ perhaloalkyl, $C_1$–$C_6$ alkenyl, $C_1$–$C_6$ alkynyl, aryl, and heteroaryl, wherein the alkyl, perhaloalkyl, alkenyl, alkynyl, aryl, are heteroaryl are optionally substituted. More preferred $R^8$ groups include hydrogen, $C_1$–$C_6$ alkyl, $C_1$–$C_6$ perhaloalkyl, $C_1$–$C_6$ alkenyl, and $C_1$–$C_6$ alkynyl. Most preferably $R^8$ is hydrogen or $C_1$–$C_6$ alkyl.

Preferred $R^9$ groups include hydrogen, $C_1$–$C_4$ alkyl, F, Cl, Br, I, $OR^2$, $NR13RI4$, and $SR^2$. More preferred $R^9$ groups include hydrogen, $C_1$–$C_4$ alkyl, F, Cl, Br, and I. Most preferably, $R^9$ is hydrogen, F, Cl, Br, or I.

Preferred $R^{10}$ groups include hydrogen, F, Cl, Br, $CF_3$, $CF_2OR^2$, $CH_2OR^2$, $OR^2$, $C_1$–$C_6$ alkyl, $C_1$–$C_6$ haloalkyl, $C_1$–$C_6$ perhaloalkyl, aryl, and heteroaryl, wherein the alkyl, haloalkyl, perhaloalkyl, aryl, and heteroaryl are optionally substituted. More preferred $R^{10}$ groups include hydrogen, F, Cl, Br, $CF_3$, $CF_2OR^2$, $CH_2OR^2$, $OR^2$, and $C_1$–$C_6$ alkyl. Most preferably, $R^{10}$ is hydrogen, F, Cl, Br, I, or $CF_3$.

Preferred $R^{11}$ groups include hydrogen, F, Cl, Br, $CF_3$, $C_1$–$C_6$ alkyl, $C_1$–$C_6$ haloalkyl, $C_1$–$C_6$ perhaloalkyl, $C_1$–$C_6$ alkenyl, $C_1$–$C_6$ alkynyl, aryl, and heteroaryl, wherein the alkyl, haloalkyl, perhaloalkyl, alkenyl, alkynyl, aryl, and heteroaryl are optionally substituted. More preferred $R^{11}$ groups include hydrogen, F, Cl, Br, I, and $C_1$–$C_4$ alkyl. Most preferably, $R^{11}$ is hydrogen, F, Cl, Br, or I.

Preferred $R^{12}$ groups include hydrogen, $C(O)R^{11}$, $SR^2$, $S(O)R^{13}$, $SO_2R^{13}$, $C_1$–$C_6$ alkyl, $C_1$–$C_6$ alkenyl, aryl, arylalkyl, and heteroaryl, wherein the alkyl, alkenyl, aryl, arylalkyl and heteroaryl are optionally substituted. More preferred $R^{12}$ groups include hydrogen, $C_1$–$C_6$ alkyl, arylalkyl, and heteroaryl, wherein the alkyl, arylalkyl and heteroaryl are optionally substituted. Most preferably, $R^{12}$ is hydrogen.

Preferred X groups include hydrogen, F, Cl, Br, I, CN, $SR^2$, $S(O)R^{13}$, $SO_2R^{13}$, $SO_3R^{13}$, $NR^{13}R^{14}$, $CF_3$, $NO_2$, and $R^{13}$. More preferred X groups include hydrogen, F, Cl, Br, I, $CF_3$ and CN.

Preferred $R^{13}$ groups include hydrogen, $C(O)R^{11}$, $SO_2R^3$, $C_1$–$C_6$ alkyl $C_1$–$C_6$ haloalkyl, $C_1$–$C_6$ perhaloalkyl, aryl, arylalkyl or heteroaryl, wherein the alkyl, haloalkyl, perhaloalkyl, aryl, arylalkyl, and heteroaryl are optionally substituted. More preferred $R^{13}$ groups include hydrogen and $C_1$–$C_6$ alkyl.

Preferred $R^{14}$ groups include hydrogen, $C(O)R^{11}$, $SO_2R^3$, $C_1$–$C_6$ alkyl $C_1$–$C_6$ haloalkyl, $C_1$–$C_6$ perhaloalkyl, aryl, arylalkyl and heteroaryl, wherein the alkyl, perhaloalkyl, aryl, arylalkyl and heteroaryl are optionally substituted. More preferred $R^{14}$ groups include hydrogen and $C_1$–$C_6$ alkyl.

In a preferred embodiment of the invention, $R^1$ is hydrogen or $C_1$–$C_4$ alkyl; $R^2$, $R^3$, $R^4$, and $R^5$ each independently is hydrogen or $C_1$–$C_6$ alkyl; $R^6$ and $R^7$ are hydrogen; $R^8$ and $R^9$ each independently is hydrogen or $C_1$–$C_6$ alkyl; $R^{10}$ is hydrogen, F, Cl, Br, I, or $CF_3$; $R^{11}$ is hydrogen, F, Cl, Br, or I; $R^{12}$ is hydrogen; and X is hydrogen, F, Cl, Br, I or CN.

In another preferred embodiment of the invention, $R^1$ is hydrogen or $C_1$–$C_4$ alkyl; $R^2$, $R^3$, $R^4$, $R^8$ each independently is hydrogen or $C_1$–$C_6$ alkyl; $R^5$, $R^6$, $R^7$, and $R^9$ are each hydrogen; $R^{10}$ is $CF_3$; $R^{11}$ is hydrogen or F; and X is hydrogen, F, Cl, Br, I or CN.

In a preferred aspect, the present invention provides a pharmaceutical composition comprising an effective amount of an androgen receptor modulating compound of formulas I or II or combinations thereof as shown above wherein $R^1$ through $R^{14}$ and X have the same definitions as given above.

In a further preferred aspect, the present invention comprises a method of modulating processes mediated by androgen receptors comprising administering to a patient an effective amount of compounds of formulas 1 or 11 or combinations thereof as shown above, wherein $R^1$ through $R^{14}$ have the same definitions as those given above.

Compounds of the present invention may be synthesized as pharmaceutically acceptable salts for incorporation into various pharmaceutical compositions. As used herein, pharmaceutically acceptable salts include, but are not limited to, hydrochloric, hydrobromic, hydroiodic, hydrofluoric, sulfuric, citric, maleic, acetic, lactic, nicotinic, succinic, oxalic, phosphoric, malonic, salicylic, phenylacetic, stearic, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl)aminomethane. Additional pharmaceutically acceptable salts are known to those skilled in the art.

AR agonist, partial agonist and antagonist compounds including compounds with tissue-selective AR modulator activity of the present invention are useful in the treatment of acne (antagonist), male-pattern baldness (antagonist), male hormone replacement therapy (agonist), wasting diseases (agonist), hirsutism (antagonist), stimulation of hematopoiesis (agonist), hypogonadism (agonist), prostatic hyperplasia (antagonist), osteoporosis (agonist), male contraception (agonist), impotence (agonist), cancer cachexia (agonist), various hormone-dependent cancers, including, without limitation, prostate (antagonist) and breast cancer and as anabolic agents (agonist). It is understood by those of skill in the art that a partial agonist may be used where agonist activity is desired, or where antagonist activity is desired, depending upon the AR modulator profile of the particular partial agonist.

It is understood by those skilled in the art that while the compounds of the present invention will typically be employed as a selective agonists, partial agonists or antagonists, that there may be instances where a compound with a mixed steroid receptor profile is preferred. For example, use of a PR agonist (i.e., progestin) in female contraception often leads to the undesired effects of increased water retention and acne flare ups. In this instance, a compound that is primarily a PR agonist, but also displays some AR and MR modulating activity, may prove useful. Specifically, the mixed MR effects would be useful to control water balance in the body, while the AR effects would help to control acne flare ups.

Furthermore, it is understood by those skilled in the art that the compounds of the present invention, including pharmaceutical compositions and formulations containing these compounds, can be used in a wide variety of combination therapies to treat the conditions and diseases described above. Thus, the compounds of the present invention can be used in combination with other hormones and other therapies, including, without limitation, chemotherapeutic agents such as cytostatic and cytotoxic agents, immunological modifiers such as interferons, interleukins, growth hormones and other cytokines, hormone therapies, surgery and radiation therapy.

Representative AR modulator compounds (i.e., agonists and antagonists) according to the present invention include:

8-chloro-1,2-dihydro-2,2,4-trimethyl-6-trifluoromethyl-9-pyrido[3,2-g]quinoline (Compound 101);

8-chloro-1,2-dihydro-1,2,2,4-tetramethyl-6-trifluoromethyl-9-pyrido [3,2-g]quinoline (Compound 102);

(R/S)-8-chloro-1,2,3,4-tetrahydro-2,2,4,10-tetramethyl-6-trifluoromethyl-9-pyrido[3,2-g]quinoline (Compound 103);

8-chloro-1,2,3,4-tetrahydro-2,2-dimethyl-6-trifluoromethyl-9-pyrido[3,2-g]quinoline (Compound 104);

8-chloro-1,2,3,4-tetrahydro-1,2,2-trimethyl-6-trifluoromethyl-9-pyrido[3,2-g]quinoline (Compound 105);

8-chloro-7-fluoro-1,2,3,4-tetrahydro-2,2,4,10-tetramethyl-6-trifluoromethyl-9-pyrido[3,2-g]quinoline (Compound 106);

8-chloro-7-fluoro-1,2,3,4-tetrahydro-2,2-dimethyl-6-trifluoromethyl-9-pyrido[3,2-g]quinoline (Compound 107);

(R/S)-8-chloro-4-ethyl-1,2,3,4-tetrahydro-6-trifluoromethyl-9-pyrido[3,2-g]quinoline (Compound 108);

(R/S)-8-chloro-4-ethyl-7-fluoro-1,2,3,4-tetrahydro-6-trifluoromethyl-9-pyrido[3,2-g]quinoline (Compound 109);

8-fluoro-1,2-dihydro-2,2,4-trimethyl-6-trifluoromethyl-9-pyrido[3,2-g]quinoline (Compound 110);

8-fluoro-1,2,3,4-tetrahydro-2,2-dimethyl-6-trifluoromethyl-9-pyrido[3,2-g]quinoline (Compound 111);

8-fluoro-1,2,3,4-tetrahydro-1,2,2-trimethyl-6-trifluoromethyl-9-pyrido[3,2-g]quinoline (Compound 112);

7,8-difluoro-1,2,3,4-tetrahydro-2,2-dimethyl-6-trifluoromethyl-9-pyrido[3,2-g]quinoline (Compound 113);

(R/S)-8-fluoro-1,2,3,4-tetrahydro-2,2,4,10-tetramethyl-6-trifluoromethyl-9-pyrido[3,2-g]quinoline (Compound 114);

7,8-difluoro-1,2,3,4-tetrahydro-2,2,4,10-tetramethyl-6-trifluoromethyl-9-pyrido[3,2-g]quinoline (Compound 115);

(R/S)-4-ethyl-8-fluoro-1,2,3,4-tetrahydro-6-trifluoromethyl-9-pyrido[3,2-g]quinoline (Compound 116);

8-bromo-1,2,3,4-tetrahydro-2,2-dimethyl-6-trifluoromethyl-9-pyrido[3,2-g]quinoline (Compound 117);

8-bromo-1,2,3,4-tetrahydro-1,2,2-trimethyl-6-trifluoromethyl-9-pyrido[3,2-g]quinoline (Compound 118);

8-bromo-7-fluoro-1,2,3,4-tetrahydro-2,2-dimethyl-6-trifluoromethyl-9-pyrido[3,2-g]quinoline (Compound 119);

(R/S)-8-bromo-1,2,3,4-tetrahydro-2,2,4,10-tetramethyl-6-trifluoromethyl-9-pyrido[3,2-g]quinoline (Compound 120);

(R/S)-8-bromo-4-ethyl-1,2,3,4-tetrahydro-6-trifluoromethyl-9-pyrido[3,2-g]quinoline (Compound 121);

1,2,3,4-tetrahydro-2,2-dimethyl-6-trifluoromethyl-9-pyrido[3,2-g]quinoline (Compound 122);

(R/S)1,2,3,4-tetrahydro-2,2,4,10-tetramethyl-6-trifluoromethyl-9-pyrido[3,2-g]quinoline (Compound 123);

1,2,3,4-tetrahydro-1,2,2-trimethyl-6-trifluoromethyl-9-pyrido[3,2-g]quinoline (Compound 124);

(R/S)-4-ethyl-1,2,3,4-tetrahydro-6-trifluoromethy1-9-pyrido[3,2-g]quinoline (Compound 125);

7-fluoro-1,2,3,4-tetrahydro-2,2-dimethyl-6-trifluoromethyl-9-pyrido[3,2-g]quinoline (Compound 126);

8-cyano-1,2,3,4-tetrahydro-2,2-dimethyl-6-trifluoromethyl-9-pyrido[3,2-g]quinoline (Compound 127);

8-cyano-1,2,3,4-tetrahydro-2,2-dimethyl-6-trifluoromethyl-9-pyrido[3,2-g]quinoline (Compound 128);

(R/S)-8-cyano-4-ethyl-1,2,3,4-tetrahydro-6-trifluoromethyl-9-pyrido[3,2-g]quinoline (Compound 129);

(R/S)-8-cyano-4-ethyl-1,2,3,4-tetrahydro-1-methyl-6-trifluoromethyl-9-pyrido[3,2-g]quinoline (Compound 130);

(R/S)-9-benzoyl-8-cyano-1,2,3,4,8,9-hexahydro-2,2-dimethyl-6-trifluoromethyl-9-pyrido[3,2-g]quinoline (Compound 131);

(R/S)-8-cyano-1,2,3,4,8,9-hexahydro-2,2-dimethyl-9-p-toluoyl-6-trifluoromethyl-9-pyrido[3,2-g]quinoline (Compound 132);

1,2,3,4-tetrahydro-2,2-dimethyl-8-methylthio-6-trifluoromethyl-9-9-pyrido[3,2-g]quinoline (Compound 134);

(R/S)-1,2,3,4-tetrahydro-2,2-dilmethyl-8-methylsulfinyl-6-trifluoromethyl-9-pyrido[3,2-g]quinoline (Compound 135);

1,2,3,4-tetrahydro-2,2-dimethyl-8-methylsulfonyl-6-trifluoromethyl-9-pyrido[3,2-g]quinoline (Compound 136);

(R/S)-7-fluoro-1,2,3,4-tetrahydro-2,2-dimethyl-6-trifluoromethyl-8-methylsulfinyl-9-pyrido[3,2-g]quinoline (Compound 137);

1,2,3,4-tetrahydro-2,2-dimethyl-8-(1-n-butylthio)-6-trifluoromethyl-9-pyrido[3,2-g]quinoline (Compound 138);

(R/S)-1,2,3,4-tetrahydro-2,2-dimethyl-8-(1-n-butylsulfinyl)-6-trifluoromethyl-9-pyrido[3,2-g]quinoline (Compound 139);

1,2,3,4-tetrahydro-2,2-dimethyl-8-(2,2,2-trifluoroethyl-1-thio)-6-trifluoromethyl-9-pyrido[3,2-g]quinoline (Compound 140);

(R/S)-4-ethyl-1,2,3,4-tetrahydro-8-methylthio-6-trifluoromethyl-9-pyrido[3,2-g]quinoline (Compound 142);

(R/S)-4-ethyl-1,2,3,4-tetrahydro-8-methylsulfinyl-6-trifluoromethyl-9-pyrido[3,2-g]quinoline (Compound 143);

1,2,3,4-tetrahydro-2,2-dimethyl-6,8-di(trifluoromethyl)-9-pyrido[3,2-g]quinoline (Compound 148);

(R/S)-4-ethyl-1,2,3,4-tetrahydro-6,8-di(trifluoromethyl)-9-pyrido[3,2-g]quinoline (Compound 149);

1,2,3,4-tetrahydro-8-(4'-methoxybenzylamino)-2,2-dimethyl-6-trifluoromethyl-9-pyrido[3,2-g]quinoline (Compound 144);

8-amino-1,2,3,4-tetrahydro-2,2-dimethyl-6-trifluoromethyl-9-pyrido[3,2-g]quinoline (Compound 145);

1,2,3,4-tetrahydro-8-methanesulfonamido-2,2-dimethyl-6-trifluoromethyl-9-pyrido[3,2-g]quinoline (Compound 146);

1,2,3,4-tetrahydro-8-bis(methanesulfon)amido-2,2-dimethyl-6-trifluoromethyl-9-pyrido[3,2-g]quinoline (Compound 147).

Schemes I–IV show examples of substitutions at the C-8 carbon of the quinolinone compounds. Compounds of the present invention, comprising classes of heterocyclic nitrogen compounds and their derivatives, may be obtained by routine chemical synthesis by those skilled in the art, e.g., by modification of the heterocyclic nitrogen compounds disclosed or by a total synthesis approach.

The sequence of steps for several general schemes to synthesize the compounds of the present invention are shown below. In each of the Schemes the R groups (e.g., $R^1$, $R^2$, etc.) correspond to the specific substitution patterns noted in the Examples. However, it is understood by those skilled in the art that other functionalities disclosed herein at the indicated positions of compounds of formulas I and II also comprise potential substituents for the analogous positions on the structures within the Schemes.

Quinoline compounds (e.g., Compound 1), employed as starting materials in Schemes I–IV are obtained by routine synthetic methods shown to those skilled in the art. Chlorosubstitution at C-8 is accomplished by treatment of a 8-pyridinoquinoline (e.g., Structure 1) with a dehydrative halogenation reagent such as phosphorous oxychloride to yield 8-chloro-9-pyridoquinolines (e.g., Structure 2) (Scheme I). 8-Fluoro-9-pyridoquinolines (3) are prepared in a halex reaction by treatment of a 8-halo-9-pyridoquinoline with an inorganic fluoride source, such as KF, in a high boiling polar solvent, such as sulpholane, at elevated temperatures.

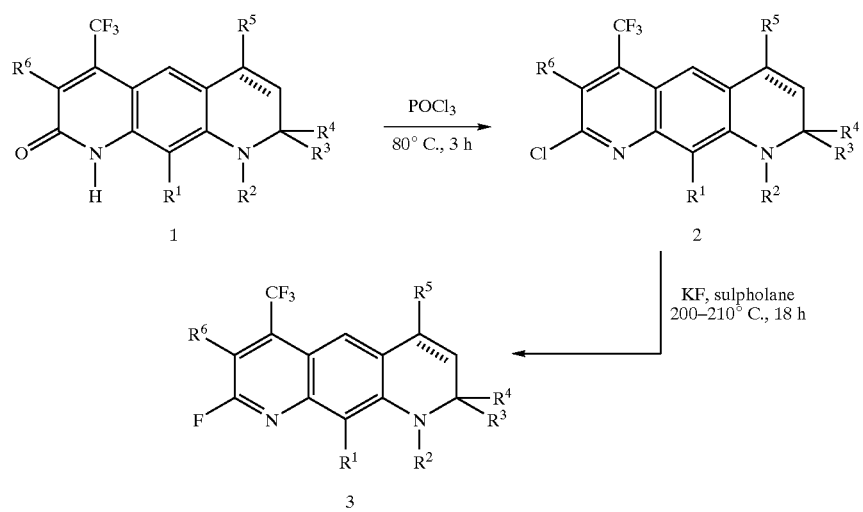

Scheme I

Analogously, 8-bromo-substitution is accomplished by treatment of a pyridonoquinoline with a dehydrative brominating reagent, such as phosphorous oxybromide to yield 8-bromo-9-pyridoquinolines (e.g., Structure 4, Scheme II). Reductive dehalogenation of the 8-position is achieved by treatment of a 8-halo-compound with a hydride source such as tri-n-butyltin hydride, in the presence of a free radical initiator, such as 2,2'-azobisisobutyronitrile (AIBN) to yield 8-hydro derivatives (e.g., Structure 5). Treatment of 8-hydro-derivatives such as Structure 5 with a nucleophilic cyanide salt, such as potassium cyanide, in the presence of para-toluenesulfonyl chloride affords 8-cyano-9-pyridoquinolines (e.g., Structure 6). Alternatively, use of an benzoic acid chloride (e.g., Structure 7), such as benzoyl chloride, in place of the para-toluenesulfonyl chloride, affords the 9-benzoyl-8-cyano-8,9-dihydro-adducts as shown in Structure 8.

Scheme II

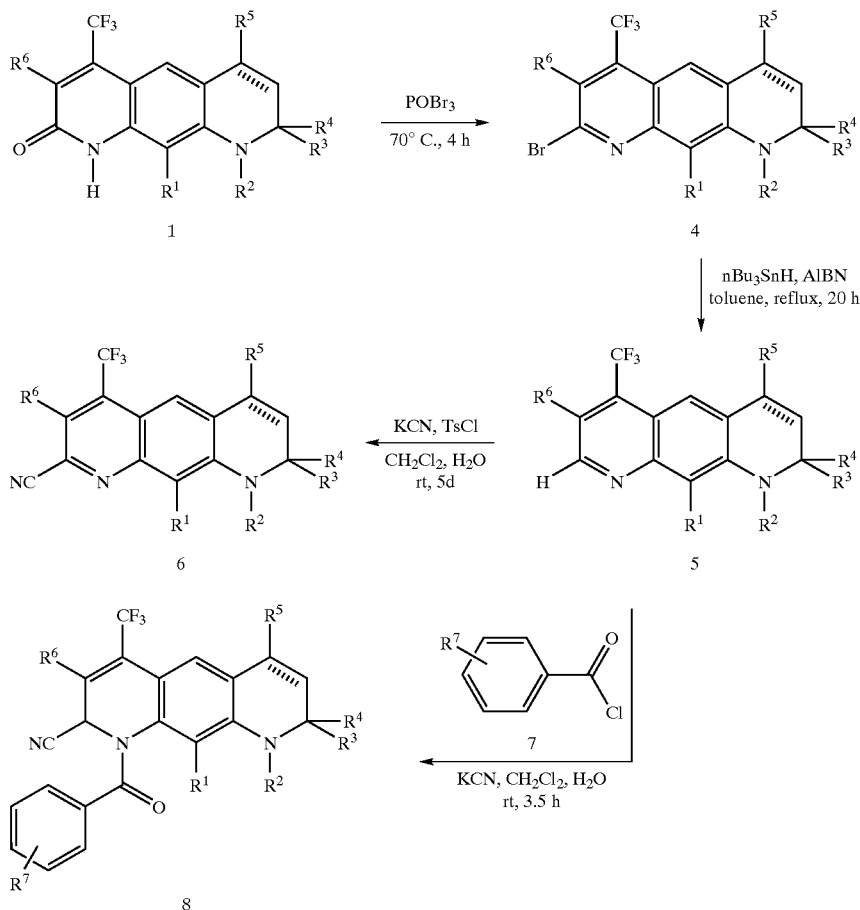

Sulfoxy or sulfonyl substitution at C-8 is introduced by a 3-step procedure from pyridonoquinolines (e.g., Structure 1, Scheme III). First, the quinoline is converted to the corresponding thiopyridonoquinoline (e.g., Structure 9) by treatment with a thionation reagent such as 2,4-bis(4-methoxyphenyl)-1,3,2,4-dithiadiphosphetane 2,4-disulfide (Lawesson's Reagent). Second, the thiopyridonoquinoline is converted to an alkylsulfide such as Structure 10 by exposure to an alkyl halide. Finally, the alkylsulfide is converted to a corresponding sulfoxide compound such as Structure 11 subsequent treatment with a mild peroxidant, such as magnesium monoperoxyphthalate (MMPP). Oxidation to a corresponding sulfone such as 12 is achieved using a stronger peroxidant, such as meta-chloroperoxybenzoic acid (mCPBA).

Scheme III

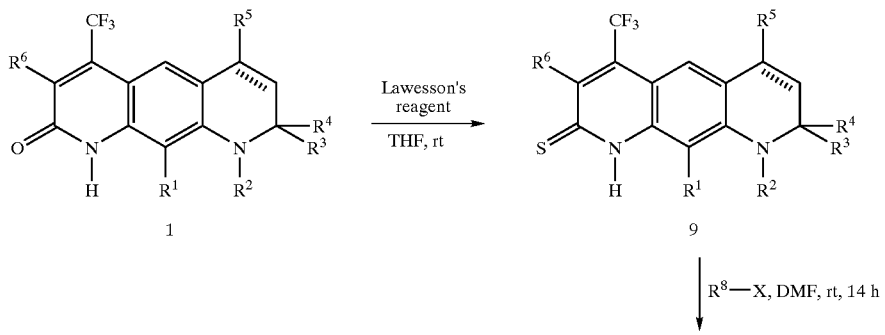

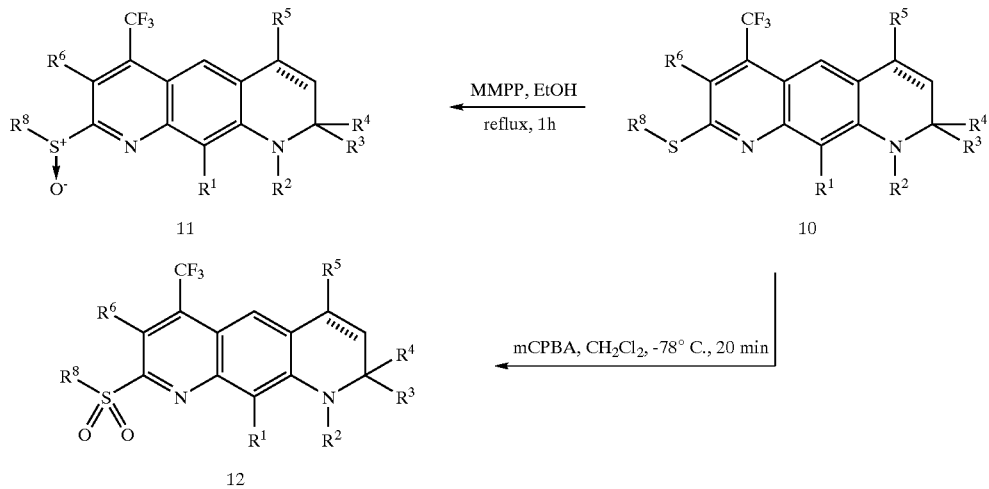

Amino-substitution at C-8 and subsequent derivatives of the 8-aminopyridoquinolines (e.g., Structure 13) are synthesized from parent 8-pyridonoquinolines (e.g., Structure 1) by treatment with an aryl or alkyl amine, such as para-methoxybenzylamine, in the presence of hexamethyldisilazane (HMDS) and an acid catalyst, such as para-toluenesulfonic acid (p-TsOH), at elevated temperatures to afford aminated products (e.g., Structure 13, as shown in Scheme IV). Removal of a benzyl protecting group is accomplished using a strong organic acid, such as trifluoroacetic acid (TFA) at elevated temperatures to afford unsubstituted aminopyridoquinolines (e.g., Structure 14). This removal is optionally performed before further derivatization, or after further derivatization, such as N-alkylation, which can be achieved by treatment with a base, such as sodium hydride, and subsequent trapping with an alkyl halide to afford mono-substituted compounds (e.g., Structure 15). Iterative alkylation by this process is achieved, leading to optionally di-substituted 8-aminopyridoquinolines (e.g., Structure 18). N-Acylations and N-sulfonylations are achieved under standard conditions, using an electrophilic acylation reagent such as acetic anhydride, or a sulfonylating reagent, such as methanesulfonyl chloride, in the presence of a mild base, such as triethylamine to afford mono or disubstituted compounds as shown in Structures 16 and 17.

Scheme IV

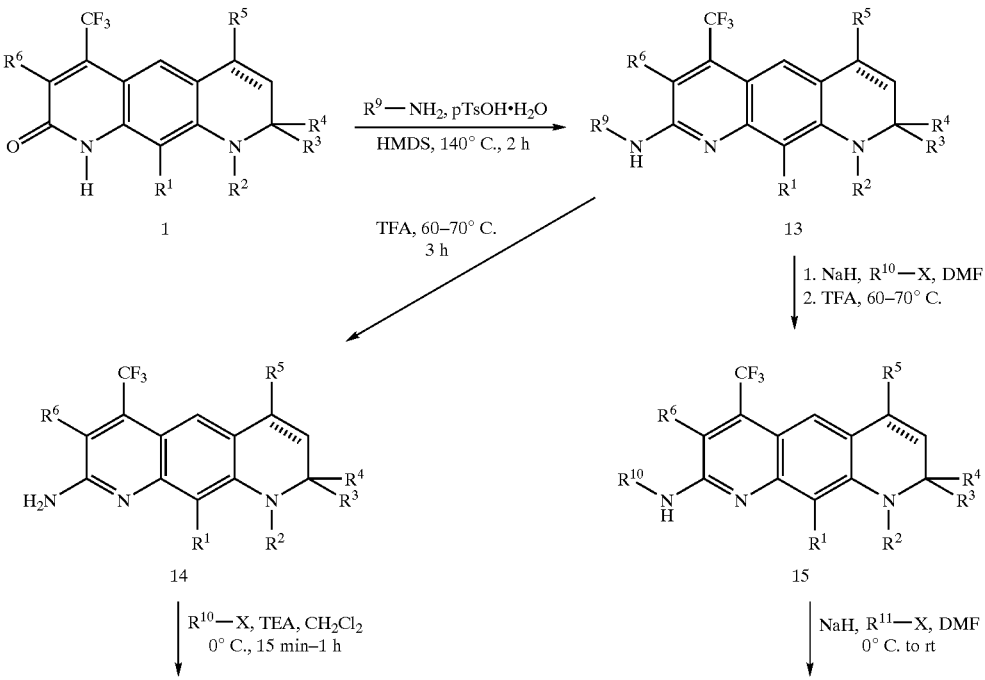

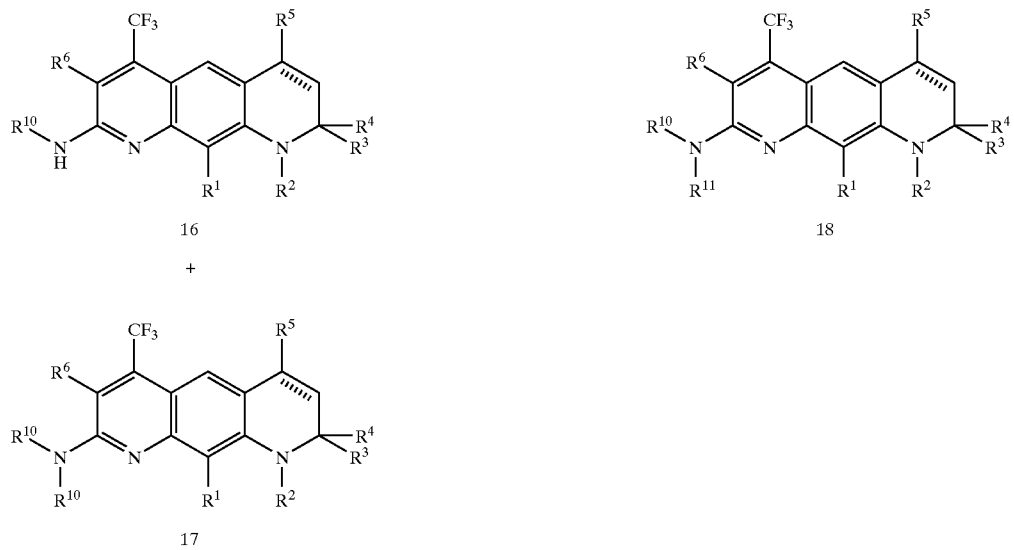

16

+

17

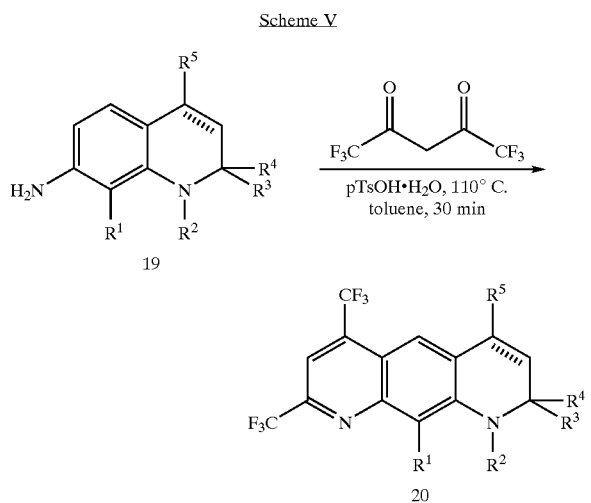

18

Scheme V shows the preparation of trifluoromethyl substituted quinolines. Trifluoromethyl-substitution at C-8 is accomplished starting with 7-amino-1,2-dihydroquinolines or a tetrahydroquinoline (e.g., Structure 19) followed by treatment with a trifluoromethyl-dione such as 1,1,1,5,5,5-hexafluoropentane-2,4-dione in the presence of an acid catalyst, such as p-TsOH, at elevated temperatures to afford 6,8-bis-trifluoromethylated compounds, an example of which is shown in Structure 20.

Scheme V

19

20

A method for alkylating amino-quinoline compounds is shown in Scheme VI. Alkylation at N-1 is achieved using standard reductive amination conditions as follows. An 8-substituted pyridoquinoline such as Structure 21, is treated with an aldehyde, such as paraformaldehyde, and a mild reductant, such as sodium cyanoborohydride, in the presence of an acid, such as acetic acid, to afford N-1-alkylated products (as shown in Structure 22, Scheme VI).

Scheme VI

21

22

The compounds of the present invention also include racemates, stereoisomers and mixtures of said compounds, including isotopically-labeled and radio-labeled compounds. Such isomers can be isolated by standard resolution techniques, including fractional crystallization and chiral column chromatography.

As noted above, any of the steroid modulator compounds of the present invention may be combined in a mixture with a pharmaceutically acceptable carrier to provide pharmaceutical compositions useful for treating the biological conditions or disorders noted herein in mammalian, and more preferably, in human patients. The particular carrier employed in these pharmaceutical compositions may take a wide variety of forms depending upon the type of administration desired, e.g., intravenous, oral, topical, suppository or parenteral.

In preparing the pharmaceutical compositions of the present invention in oral liquid dosage forms (e.g., suspensions, elixirs and solutions), typical pharmaceutical media such as water, glycols, oils, alcohols, flavoring agents, preservatives, coloring agents and the like may be employed. Similarly, when preparing oral solid dosage forms (e.g., powders, tablets and capsules), carriers such as starches, sugars, diluents, granulating agents, lubricants, binders, disintegrating agents and the like may be employed. Due to their ease of administration, tablets and capsules represent the most advantageous oral dosage form for the pharmaceutical compositions of the present invention.

For parenteral administration, a carrier will typically comprise sterile water although other ingredients that aid in solubility or serve as preservatives, may also be included. Furthermore, injectable suspensions may also be prepared in which case appropriate liquid carriers, suspending agents and the like may be employed.

For topical administration compounds of the present invention may be formulated using bland moisturizing bases such as ointments or creams. Examples of suitable ointment bases are petrolatum, petrolatum plus volatile silicones, lanolin, and water in oil emulsions such as Eucerin™ (Beiersdorf). Examples of suitable cream bases are Nivea™ Cream (Beiersdorf), cold cream (USP), Purpose Cream™ (Johnson & Johnson), hydrophilic ointment (USP), and Lubriderm™ (Warner-Lambert).

The pharmaceutical compositions and compounds of the present invention may generally be administered in the form of a dosage unit (e.g., tablet, capsule etc.) at concentrations from about 1 μg/kg of body weight to about 500 mg/kg of body weight, more preferably from about 10 μg/kg to about 250 mg/kg, and most preferably from about 20 μg/kg to about 100 mg/kg. As recognized by those skilled in the art, the particular quantity of pharmaceutical composition according to the present invention administered to a patient will depend upon a number of factors, including, without limitation, the biological activity desired, the condition of the patient, and tolerance for the drug.

The compounds of this invention also have utility when radio- or isotopically-labeled as ligands for use in assays to determine the presence of AR in a cell background or extract. They are particularly useful due to their ability to selectively activate androgen receptors, and can therefore be used to determine the presence of such receptors in the presence of other steroid receptors or related intracellular receptors.

Due to the selective specificity of the compounds of this invention for steroid receptors, these compounds can be used to purify samples of steroid receptors in vitro. Such purification can be carried out by mixing samples containing steroid receptors with one or more of the compounds of the present invention so that the compounds bind to the receptors of choice, and then separating out the bound ligand/receptor combination by separation techniques which are known to those of skill in the art. These techniques include column separation, filtration, centrifugation, tagging and physical separation, and antibody complexing, among others.

The compounds and pharmaceutical compositions of the present invention may advantageously be used in the treatment of the diseases and conditions described herein. In this regard, the compounds and compositions of the present invention are particularly useful as modulators of male sex steroid-dependent diseases and conditions such as the treatment of acne, male-pattern baldness, male hormone replacement therapy, wasting diseases, hirsutism, stimulation of hematopoiesis, hypogonadism, prostatic hyperplasia, osteoporosis (agonist), male contraception (agonist), impotence (agonist), cancer cachexia (agonist), various hormone-dependent cancers including without limitation prostate cancer and breast cancer, and as anabolic agents.

The compounds and pharmaceutical compositions of the present invention possess a number of advantages over previously identified steroidal and non-steroidal compounds. Furthermore, the compounds and pharmaceutical compositions of the present invention possess a number of advantages over previously identified steroid modulator compounds. For example, the compounds are extremely potent AR activators preferably displaying 50% maximal activation of AR at a concentration of less than 100 nM, more preferably at a concentration of less than 50 nM, more preferably yet at a concentration of less than 20 nM, and most preferably at a concentration of 10 nM or less. Also, the selective compounds of the present invention generally do not display undesired cross-reactivity with other steroid receptors, as is seen with the compound mifepristone (RU486; Roussel Uclaf). Mifepristone is a known PR antagonist that displays an undesirable cross reactivity on GR and AR, thereby limiting its use in long-term, chronic administration. In addition, the small organic molecules of the present invention are easier to synthesize, provide greater stability and are more easily administered in oral dosage forms than other known steroidal compounds.

The invention is further illustrated by reference to the following non-limiting Examples.

General Experimental Chemical Procedures. Proton nuclear magnetic resonance ($^1$H NMR) spectra were recorded on a Brüker AC 400. Chemical shifts are given in parts per million (ppm) downfield from internal reference tetramethylsilane in δ-units, and coupling constants (J-values) are given in hertz (Hz). Selected data are reported in the following manner: chemical shift, multiplicity, coupling constants, and assignment. Melting points were taken on an Electrothermal IA91 00 Digital apparatus and are uncorrected. "Brine" refers to a saturated aqueous solution of NaCl. Unless otherwise specified, solutions of common inorganic salts used in work-ups are aqueous solutions. All moisture sensitive reactions were carried out using oven-dried or flame-dried round-bottomed (r.b.) flasks and glassware under an atmosphere of dry nitrogen.

EXAMPLE 1

8–Chloro-1,2-dihydro-2,2,4-trimethyl-6-trifluoromethyl-9-pyrido[3,2-g]quinoline (Compound 101, Structure 2 of Scheme I, where $R^1=R^2=R^6=H$, $R^3=R^4=R^5=Me$). General Procedure for the Preparation of 8-Chloro-Derivatives. To an oven-dried 10-mL r.b. flask containing 1,2-dihydro-2,2,4-trimethyl-6-trifluoromethyl-8-pyridono[5,6-g]quinoline (0.144 g, 0.467 mmol) was added 1.0 mL phosphorous oxychloride, and the mixture was heated to reflux for 3 h. Upon cooling to room temperature, the reaction mixture was poured over 50 g ice, and extracted with 50 mL EtOAc. The organic layer was washed with saturated $NaHCO_3$ (3×25 mL), dried ($Na_2SO_4$), and concentrated under reduced pressure. The residue was purified by flash column chromatography (silica gel, hexanes/EtOAc, 1:1) to give 146 mg (96%) of the desired 8-chloropyridoquinoline as a bright yellow solid. Data for Compound 101: $^1$H NMR (400 MHz, CDCl$_3$) 7.61 (br s, 1H, 5-H), 7.24 (s, 1H, 7-H), 6.85 (s, 1H, 10-H), 5.63 (s, 1H, 3-H), 4.51 (br s, 1H, NH), 2.10 (d, 3H, J=1.1, 4-CH$_3$), 1.37 [s, 6H, 2-(CH$_3$)$_2$].

EXAMPLE 2

8-Chloro-1,2-dihydro-1,2,2,4-tetramethyl-6-trifluoromethyl-9-pyrido-[3,2-q]quinoline (Compound 102, Structure 22 of Scheme VI, where R$^1$=R$^6$=H, R$^3$=R$^4$=R$^5$=Me, X=Cl). To an oven-dried 50-mL r.b. flask containing 8-chloro-1,2-dihydro-2,2,4-trimethyl-6-trifluoromethyl8-pyridono[5,6-g]quinoline (76 mg, 0.23 mmol) in 3.0 mL HOAC at room temperature was added paraformaldehyde (80 mg) and NaCNBH$_3$ (157 mg, 2.30 mmol, 10.0 equiv), and the mixture was allowed to stir overnight. The reaction mixture was then added to 50 mL saturated NaHCO$_3$ and extracted with EtOAc (2×50 mL). The organic layer was dried (Na$_2$SO$_4$) and concentrated under reduced pressure. Purification by flash column chromatography (silica gel, hexane/EtOAc, 4:1) afforded 72 mg (91%) of the methylated product as a yellow solid. Data for Compound 102: $^1$H NMR (400 MHz, CDCl$_3$) 7.56 (s, 1H, 5-H), 7.26 (s, 1H, 7-H), 6.88 (s, 1H, 10-H), 5.61 (s, 1H, 3-H), 2.93 (s, 3H, N—CH$_3$), 2.10 (s, 3H, 4-CH$_3$), 1.41 [s, 6H, 2-(CH$_3$)$_2$].

EXAMPLE 3

(R/S)-8-Chloro-1,2,3,4-tetrahydro-2,2,4,10-tetramethyl-6-trifluoromethyl-9-pyrido[3,2-g]quinoline (Compound 103. Structure 2 of Scheme I, where R$^1$=R$^3$=R$^4$=R$^5$=Me, R$^2$=R$^6$=H). This compound was prepared from 1,2,3,4-tetrahydro-2,2,4,10-tetramethyl-6-trifluoromethyl-8-pyridono[5,6-g]quinoline (0.127 g, 0.393 mmol) in the manner previously described for Compound 101 affording 125 mg (93%) of the desired chloropyridine as a bright yellow solid. Data for Compound 103: $^1$H NMR (400 MHz, CDCl$_3$) 7.75 (br s, 1H, 5-H), 7.28 (s, 1H, 7-H), 4.21 (br s, 1H, NH), 3.11 (ddq, 1H, J=12.9, 12.4, 6.3, 4-H), 2.47 (s, 3H, 10-CH$_3$), 1.84 and 1.53 [dd of ABq, 2H, J$_{AB}$=13.0, J$_A$=5.1, 1.6 (3-H$_{eq}$), J$_B$=12.9, 0 (3-H$_{ax}$)], 1.47 (d, 3H, J=6.7, 4-CH$_3$), 1.38 and 1.29 [2s, 2×3H, 2-(CH$_3$)$_2$].

EXAMPLE 4

8–Chloro-1,2,3,4-tetrahydro-2,2-dimethyl-6-trifluoromethyl-9-pyrido[3,2-g]quinoline (Compound 104, Structure 2 of Scheme I, where R$^1$=R$^2$=R$^5$=R$^6$=H, R$^3$=R$^4$=Me). This compound was prepared from 1,2,3,4-tetrahydro-2,2-dimethyl-6-trifluoromethyl-8-pyrido[5,6-g]quinoline (4.00 g, 13.5 mmol) in the manner previously described for Compound 101 affording 3.99 g (94%) of the desired chloropyridine as a bright yellow solid. Data for Compound 104: $^1$H NMR (400 MHz, CDCl$_3$) 7.66 (s, 1H, 5-H), 7.25 (s, 1H, 7-H), 6.91 (s, 1H, 10-H), 4.43 (br s, 1H, NH), 3.00 (t, 2H, J=6.7, 4-H), 1.81 (t, 2H, J=6.7, 3-H), 1.31 [s, 6H, 2-(CH$_3$)$_2$].

EXAMPLE 5

8-Chloro-1,2,3,4-tetrahydro-1,2,2-trimethyl-6-trifluoromethyl-9-pyrido[3,2-g]quinoline (Compound 105, Structure 22 of Scheme VI, where R$^1$=R$^5$=R$^6$=H, R$^3$=R$^4$=Me). This compound was prepared from 8-chloro-1,2,3,4-tetrahydro-2,2-dimethyl-6-trifluoromethyl8-pyridono[5,6-g]quinoline (0.100 g, 0.300 mmol) in the manner previously described for Compound 102, affording 95 mg (91%) of the desired methylation product as a bright yellow solid. Data for Compound 105: $^1$H NMR (400 MHz, CDCl$_3$) 7.58 (s, 1H, 5-H), 7.27 (s, 1H, 7-H), 6.99 (s, 1H, 10-H), 2.95 (s, 3H, NCH$_3$), 2.93 (t, 2H, J=6.6, 4-H), 1.88 (t, 2H, J=6.4, 3-H), 1.33 [s, 6H, 2-(CH$_3$)$_2$].

EXAMPLE 6

8-Chloro-7-fluoro-1,2,3,4-tetrahydro-2,2,4,10-tetramethyl-6-trifluoro-methyl-9-pyrido[3,2-g]quinoline (Compound 106, Structure 2 of Scheme I, where R$^1$=R$^3$=R$^4$=R$^5$=Me, R$^2$=H, R$^6$=F). This compound was prepared from 7-fluoro-1,2,3,4-tetrahydro-2,2,4,10-tetramethyl-6-trifluoromethyl-8-pyridono[5,6-g]quinoline (0.085 g, 0.248 mmol) in the manner previously described for Compound 101, affording 74 mg (83%) of the desired methylation product as a bright yellow solid. Data for Compound 106: $^1$H NMR (400 MHz, CDCl$_3$) 7.77 (s, 1H, 5-H), 4.11 (br s, 1H, 1-H), 3.11 (m, 1H, 4-H), 2.46 (s, 3H, 10-CH$_3$), 1.87 (ddd, 1H, J=12.9, 5.0, 1.6, 3-H$_{eq}$), 1.53 (dd, 1H, J=13.0, 12.8, 3-H$_{ax}$), 1.47 (d, 3H, J=6.6, 4-CH$_3$), 1.38 and 1.29 [2s, 2×3H, 2-(CH$_3$)$_2$].

EXAMPLE 7

8-Chloro-7-fluoro-1,2,3,4-tetrahydro-2,2-dimethyl-6-trifluoromethyl-9-pyrido[3,2-g]quinoline (Compound 107, Structure 2 of Scheme I, where R$^1$=R$^2$=R$^5$=H, R$^3$=R$^4$=Me, R$^6$=F). This compound was prepared from 7-fluoro-1,2,3,4-tetrahydro-2,2-dimethyl-6-trifluoromethyl-8-pyridono[5,6-g]quinoline (0.302 g, 0.961 mmol) in the manner previously described for Compound 101, affording 310 mg (97%) of the desired chloropyridine as a bright yellow solid. Data for Compound 107: $^1$H NMR (400 MHz, CDCl$_3$) 7.69 (br s, 1H, 5-H), 6.89 (s, 1H, 10-H), 4.36 (br s, 1H, NH), 3.01 (dd, 2H, J=6.7, 6.6, 3-H), 1.80 (dd, 2H, J=6.7, 6.7, 2-H), 1.30 [s, 6H, 2-(CH$_3$)$_2$].

EXAMPLE 8

(R/S)-8-Chloro-4-ethyl-1,2,3,4-tetrahydro-6-trifluoromethyl-9-pyrido[3,2-g]guinoline (Compound 108, Structure 2 of Scheme I, where R$^1$=R$^2$=R$^3$=R$^4$=R$^6$=H, R$^5$=Et). This compound was prepared from 4-ethyl-1,2,3,4-tetrahydro-6-trifluoromethyl-8-pyridono[5,6-g]quinoline (0.326 g, 1.11 mmol) in the manner previously described for Compound 101, affording 311 mg (90%) of the desired chloropyridine as a bright yellow solid. Data for Compound 108: $^1$H NMR (400 MHz, CDCl$_3$) 7.64 (br s, 1H, 5-H), 7.27 (s, 1H, 7-H) 6.93 (d, 1H, J=2.3, 10-H), 4.66 (br s 1H, NH), 3.45 (m, 2H, 2-H), 2.87 (m, 1H, 4-H), 1.96 (m, 2H, 3-H), 1.70 (m, 2H, 4-CH$_2$CH$_3$), 1.02 (t, 3H, J=7.4, 4-CH$_2$CH$_3$).

EXAMPLE 9

(R/S)-8-Chloro-4-ethyl-7-fluoro-1,2,3,4-tetrahydro-6-trifluoromethyl-9-pyrido[3,2-g]guinoline (Compound 109, Structure 2 of Scheme I, where R$^1$=R$^2$=R$^3$=R$^4$=H, R$^5$=Et, R$^6$=F). This compound was prepared from 4-ethyl-7-fluoro- 1,2,3,4-tetrahydro-6-trifluoromethyl-8-pyridono[5,6-g] quinoline (0.326 g, 1.11 mmol) in the manner previously described for Compound 101, affording 311 mg (90%) of the desired chloropyridine as a bright yellow solid. Data for Compound 109: $^1$H NMR (400 MHz, CDCl$_3$) 7.68 (s, 1H, 5-H), 6.91 (s, 1H, 10-H), 4.62 (br s, 1H, NH), 3.46 (m, 2H, 2-H), 2.87 (m, 1H, 4-H), 1.94 (m, 2H, 3-H), 1.69 (m, 2H, 4-CH$_2$CH$_3$), 102 (t, 3H, J=7.4, 4-CH$_2$CH$_3$).

EXAMPLE 10

8-Fluoro-1,2-dihydro-2,2,4-trimethyl-6-trifluoromethyl-9-pyrido[3,2-g]quinoline (Compound 110, Structure 3 of Scheme I, where $R^1=R^2=R^6=H$, $R^3=R^4=R^5=Me$). General Procedure for Preparation of 8-Fluoro-Derivatives. To a 10-mL r.b. flask containing 8-chloro-1,2-dihydro-2,2,4-trimethyl-6-trifluoromethyl-9-pyrido[3,2-g]quinoline (101 mg, 0.309 mmol) in 0.8 mL sulpholane was added anhydrous potassium fluoride (180 mg, 3.09 mmol, 10.0 equiv), and the mixture was heated to 200–210 C for18 h. Upon cooling to room temperature, the mixture was diluted with 25 mL EtOAc, and the organic layer was washed with water (10 mL) and brine (10 mL), dried (Na$_2$SO$_4$) and concentrated under reduced pressure. Purification by flash column chromatography (silica gel, hexane/EtOAc, 4:1) afforded 88 mg (98%) of the desired 8-fluoropyridoquinoline as a bright yellow solid. Data for Compound 110: $^1$H NMR (400 MHz, CDCl$_3$) 7.64 (d, 1H, J=1.5, 5-H), 6.95 (d, 1H, J=1.1, 7-H), 6.78 (s, 1H, 10-H), 5.61 (s, 1H, 3-H), 4.37 (br s, 1H, Nm), 2.11 (d, 3H, J=1.0, 4-CH$_3$), 1.38 [s, 6H, 2-(CH$_3$)$_2$].

EXAMPLE 11

8-Fluoro-1,2,3,4-tetrahydro-2,2-dimethyl-6-trifluoromethyl-9-pyrido[3,2-g]quinoline (Compound 111, Structure 3 of Scheme I, where $R^1=R^2=R^5=R^6H$, $R^3=R^4=$Me). This compound was prepared from 8-chloro-1,2,3,4-tetrahydro-2,2-dimethyl-6-trifluoromethyl-9-pyrido[3,2-g]quinoline (200 mg, 0.63 mmol) in the manner previously described for Compound 110, affording 167 mg (89%) of the desired 8-fluoro adduct as a bright yellow solid. Data for Compound 111: $^1$H NMR (400 MHz, CDCl$_3$) 7.67 (br s, 1H, 7-H), 6.96 (d, 1H, J=2.2, 7-H), 6.84 (s, 1H, 10-H), 4.44 (br s, 1H, NH), 3.00 (dd, 2H, J=6.7, 6.6, 3-H), 1.80 (dd, 2H, J=6.7, 6.7, 2-H), 1.30 [s, 6H, 2-(CH$_3$)$_2$].

EXAMPLE 12

8-Fluoro-1,2,3,4-tetrahydro-1,2,2-trimethyl-6-trifluoromethyl-9-pyrido[3,2-g]quinoline (Compound 112. Structure 22 of Scheme VI, where $R^1=R^5=R^6=H$, $R^3=R^4=$Me, X=F). This compound was prepared from 8-fluoro-1,2,3,4-tetrahydro-2,2-dimethyl-6-trifluoromethyl-9-pyrido[3,2-g]quinoline (87 mg, 0.29 mmol) in the manner previously described for Compound 102, affording 71 mg (78%) of the desired N-methylated compound as a bright yellow solid. Data for Compound 112: $^1$H NMR (400 MHz, CDCl$_3$) 7.59 (br s, 1H, 5-H), 6.96 (d, 1H, J=2.3, 7-H), 6.91 (s, 1H, 10-H), 2.96 (s, 3H, N—CH$_3$), 2.93 (dd, 2H, J=6.5, 6.5, 3-H), 1.89 (dd, 2H, J=6.7, 6.3, 2-H), 1.33 [s, 6H, 2-(CH$_3$)$_2$].

EXAMPLE 13

7,8-Difluoro-1,2,3,4-tetrahydro-2,2-dimethyl-6-trifluoromethyl-9-pyrido[3,2-g]quinoline (Compound 113. Structure 3 of Scheme I, where $R^1=R^2=R^5=H$, $R^3=R^4=Me$, $R^6=F$). This compound was prepared from 8-chloro-7-fluoro-1,2,3,4-tetrahydro-2,2-dimethyl-6-trifluoromethyl-9-pyrido[3,2-g]quinoline (301 mg, 0.901 mmol) in the manner previously described for Compound 110, affording 237 mg (83%) of the desired 8-fluoro adduct as a bright yellow solid. Data for Compound 113: $^1$H NMR (400 MHz, CDCl$_3$) 7.70 (br s, 1H, 5-H), 6.72 (s, 1H, 10-H), 4.20 (br s, 1H, NH), 3.00 (dd, 2H, J=6.7, 6.6, 3-H), 1.79 (dd, 2H, J=6.7, 6.7, 2-H), 1.27 [s, 6H, 2-(CH$_3$)$_2$].

EXAMPLE 14

(R/S)-8-Fluoro-1,2,3,4-tetrahydro-2,2,4,10-tetramethyl-6-trifluoromethyl-9-tpyrido[3,2-g]quinoline (Compound 114, Structure 3 of Scheme I, where $R^1=R^3=R^4=R^5=Me$, $R^2=R^6=H$). This compound was prepared from (R/S)-8-chloro-1,2,3,4-tetrahydro-2,2,4,10-tetramethyl-6-trifluoromethyl-9-pyrido[3,2-g]quinoline (49 mg, 0.14 mmol) in the manner previously described for Compound 110, affording 41 mg (90%) of the desired 8-fluoro adduct as a bright yellow solid. Data for Compound 114: $^1$H NMR (400 MHz, CDCl$_3$) 7.77 (s, 1H, 5-H), 6.98 (d, 1H, J=2.8, 7-H), 4.09 (br s, 1H, 1-H), 3.11 (m, 1H, 4-H), 2.41 (s, 3H, 10-CH$_3$), 1.87 (ddd, 1H, J=12.9, 5.1, 1.6, 3-H$_{eq}$), 1.53 (dd, 1H, J=13.0, 12.8, 3-H$_{ax}$), 1.48 (d, 3H, J=6.6, 4-CH$_3$), 1.35 and 1.29 [2s, 2×3H, 2-(CH$_3$)$_2$].

EXAMPLE 15

7,8-Difluoro-1,2,3,4-tetrahydro-2,2,4,10-tetramethyl-6-trifluoromethyl-9-pyrido[3,2-g]quinoline (Compound 115. Structure 3 of Scheme I, where $R^1=R^3=R^4=R^5=Me$, $R^2=H$, $R^6=F$). This compound was prepared from 8-chloro-7-fluoro-1,2,3,4-tetrahydro-2,2,4,10-tetramethyl-6-trifluoromethyl-9-pyrido[3,2-g]quinoline (15 mg, 0.04 mmol) in the manner previously described for Compound 110, affording 13 mg (91%) of the desired 8-fluoro adduct as a bright yellow solid. Data for Compound 115: $^1$H NMR (400 MHz, CDCl$_3$) 7.78 (s, 1H, 5-H), 4.11 (br s, 1H, 1-H), 3.11 (m, 1H, 4-H), 2.46 (s, 3H, 10-CH$_3$), 1.87 (ddd, 1H, J=12.9, 5.0, 1.6, 3-H$_{eq}$), 1.53 (dd, 1H, J=13.0, 12.8, 3-H$_{ax}$), 1.47 (d, 3H, J=6.6, 4-CH$_3$), 1.38 and 1.29 [2s, 2×3H, 2-(CH$_3$)$_2$].

EXAMPLE 16

(R/S)-4-Ethyl-8-fluoro-1,2,3,4-tetrahydro-6-trifluoromethyl-9-pyrido[3,2-g]quinoline (Compound 116. Structure 3 of Scheme I, where $R^1=R^2=R^3=R^4=R^6=H$, $R^5$Et). This compound was prepared from (R/S)-8-chloro-4-ethyl-1,2,3,4-tetrahydro-6-trifluoromethyl-9-pyrido[3,2-g]quinoline (452 mg, 1.44 mmol) in the manner previously described for Compound 110, affording 411 mg (96%) of the desired 8-fluoro adduct as a bright yellow solid. Data for Compound 116: $^1$H NMR (400 MHz, CDCl$_3$) 7.65 (br s, 1H, 5-H) 6.96 (d, 1H, J=2.3, 7-H), 6.85 (s, 1H, 10-H), 4.66 (br s, 1H, NH), 3.44 (m, 2H, 2-H), 2.87 (m, 1H, 4-H), 1.96 (m, 2H, 3-H), 1.70 (m, 2H, 4-CH$_2$CH$_3$), 1.03 (t, 3H, J=7.4, 4-CH$_2$CH$_3$).

EXAMPLE 17

8-Bromo-1,2,3,4-tetrahydro-2,2-dimethyl-6-trifluoromethyl-9-pyrido[3,2-g]quinoline (Compound 117, Structure 4 of Scheme II, where $R^1=R^2=R^5=R^6=H$, $R^3R^4=$Me). General Procedure for the Preparation of 8-Bromo-Derivatives. To a flame-dried 25 mL r.b. flask, phosphorous oxybromide (2.0 g, 7.0 mmol, mp 56 C) and 1,2,3,4-tetrahydro-2,2-dimethyl-6-trifluoromethyl-9-pyrido[3,2-g] quinoline (500 mg, 1.59 mmol) was added in a glove bag under $N_2$. The resultant mixture was heated up to 60 C and allowed to stir for 2.5 h. The reaction was allowed to cool to room temperature and slowly quenched with ice and EtOAc. The mixture was then poured into ice (50 g) and EtOAc (50 mL) and stirred for 10 min. The layers were separated, and the aqueous layer was neutralized with saturated $NaHCO_3$ and extracted with EtOAc (3×50 mL). The combined organic layers were washed with water (20 mL), saturated $NaHCO_3$ (20 mL), and brine (5 mL), dried ($Na_2SO_4$), and concentrated under reduced pressure to yield a dark orange solid. Purification by flash column chromatography (silica gel, hexanes/EtOAc, 2:1) followed by recrystallization of the resultant solid from hot EtOAc afforded 455 mg (80%) of the bromoquinoline 117 as yellow crystals. Data for Compound 117: $^1$H NMR (400 MHz, $CDCl_3$) 7.65 (s, 1H, 5-H), 7.38 (s, 1H, 7-H), 6.92 (s, 1H, 10-H), 4.43 (br s, 1H, NH), 2.99 (t, 2H, J=6.3, 4-H), 1.81 (t, 2H, J=6.7, 3-H), 1.31 [s, 6H, 2-$(CH_3)_2$].

EXAMPLE 18

8-Bromo-1,2,3,4-tetrahydro-1,2,2-trimethyl-6-trifluoromethyl-9-pyrido[3,2-g]quinoline (Compound 118. Structure 22 of Scheme VI, where $R^1=R^5=R^6=H$, $R^3=R^4=$Me, X=Br). This compound was prepared from Compound 117 (38 mg, 101 μmol) in the manner previously described for Compound 102, affording 31 mg (79%) of the alkylated bromoquinoline as a yellow solid. Data for Compound 118: $^1$H NMR (400 MHz, $CDCl_3$) 7.57 (s, 1H, 5-H), 7.39 (s, 1H, 7-H), 7.01 (s, 1H, 10-H), 2.98 (s, 3H, $NCH_3$), 2.92 (t, 2H, J=6.2, 4-H), 1.88 (t, 2H, J=6.5, 3-H), 1.33 [s, 6H, 2-$(CH_3)_2$].

EXAMPLE 19

8-Bromo-7-fluoro-1,2,3,4-tetrahydro-2,2-dimethyl-6-trifluoromethyl-9-pyrido[3,2-g]quinoline (Compound 119, Structure 4 of Scheme II, where $R^1=R^2=R^5=H$, $R^3=R^4=$Me, $R^6=$F). This compound was prepared from 7-fluoro-1,2,3,4-tetrahydro-2,2-dimethyl-6-trifluoromethyl-8-pyridono[5,6-g]quinoline (276 mg, 0.88 mmol) in the manner previously described for Compound 117, affording 285 mg (86%) of the desired product as a yellow solid. Data for Compound 119: $^1$H NMR (400 MHz, $CDCl_3$) 7.69 (s, 1H, 5-H), 6.91 (s, 1H, 10-H), 4.11 (br s, 1H, 1-H), 3.00 (t, 2H, J=6.6, 4-H), 1.80 (t, 2H, J=6.7, 3-H), 1.30 [s, 6H, 2-$(CH_3)_2$].

EXAMPLE 20

(R/S)-8-Bromo-1,2,3,4-tetrahydro-2,2,4,10-tetramethyl-6-trifluoromethyl-9-pyrido[3,2-g]quinoline (Compound 120. Structure 4 of Scheme II, where $R^1=R^3=R^4=R^5=$Me, $R^2=R^6=$H). This compound was prepared from 1,2,3,4-tetrahydro-2,2,4,10-tetramethyl-6-trifluoromethyl-9-pyrido[3,2-g]quinoline (300 mg, 0.92 mmol) in the manner previously described for Compound 117, affording 335 mg (93%) of the desired product as a yellow solid. Data for Compound 120: $^1$H NMR (400 MHz, $CDCl_3$) 7.74 (br s, 1H, 5-H), 7.40 (s, 1H, 7-H), 4.20 [br s, 1H, $(CH_3)_2CNH$], 3.10 (m, 1H, 4-H), 2.47 (s, 3H, 10-$CH_3$), 1.88 and 1.53 [d of Abq, 2H, $J_{AB}$=13.0, $J_A$=5.0 (3-$H_{eq}$), $J_B$=12.9 (3-$H_{ax}$)], 1.48 (d, 3H, J=6.7, 4-$CH_3$), 1.38 and 1.29 [2s, 2×3H, 2-$(CH_3)_2$].

EXAMPLE 21

(R/S)-8-Bromo-4-ethyl-1,2,3,4-tetrahydro-6-trifluoromethyl-9-pyrido[3,2-g]quinoline (Compound 121, Structure 4 of Scheme II, where $R^1=R^2=R^3=R^4=R^6=H$, $R^5=$Et). This compound was prepared from 4-ethyl-1,2,3,4-tetrahydro-6-trifluoromethyl-9-pyrido[3,2-g]quinoline (125 mg, 397 μmol) in the manner previously described for Compound 117, affording 130 mg (91%) of Compound 121 as a fluorescent yellow-orange solid. Data for Compound 121: $^1$H NMR (400 MHz, $CDCl_3$) 7.63 (s, 1H, 5-H), 7.38 (s, 1H, 7-H), 6.94 (s, 1H, 10-H), 4.67 (br s, 1H, NH), 3.43 (m, 2H, 2-H), 2.86 (m, 1H, 4-H), 1.99 (m, 2H, 3-H), 1.70 (m, 2H, 4-$CH_2CH_3$), 1.02 (t, 3H, J=7.5, 4-$CH_2CH_3$).

EXAMPLE 22

1,2,3,4-Tetrahydro-2,2-dimethyl-6-trifluoromethyl-9-pyrido[3,2-g]quinoline (Compound 122. Structure 5 of Scheme II, where $R^1=R^5=R^6=H$, $R^2=R^3=R^4=$Me). General Procedure for the Preparation of 8-Hydro-Derivatives. To a flame-dried r.b. flask, tributyltin hydride (3.75 mL, 13.9 mmol) was dissolved in toluene (5 mL) and brought to reflux. To this reaction solution was added a mixture of 8-bromo-1,2,3,4-tetrahydro-2,2-dimethyl-6-trifluoromethyl-9-pyrido[3,2-g]quinoline (1.25 g, 3.48 mmol) and 2,2'-azobisisobutyrontrile suspended in toluene (20 mL) dropwise over 20 min. The reaction mixture was then refluxed for 20 h. Carbon tetrachloride (5 mL) was added to the reaction and was stirred at room temperature for 2.5 h. The toluene was evaporated under reduced pressure. The resulting solid was suspended in hexanes and filtered through a Buchner finnel. Copious washes with hexanes yielded 750 mg (77%) of quinoline 122 as a bright yellow powder. Data for Compound 122: $^1$H NMR (400 MHz, $CDCl_3$) 8.74 (d, 1H, J=4.4, 8-H), 7.71 (s, 1H, 5-H), 7.29 (d, 1H, J=4.6, 7-H), 7.03 (s, 1H, 10-H), 4.35 (br s, 1H, NH), 3.05 (t, 2H, J=6.3, 4-H), 1.82 (t, 2H, J=6.7, 3-H), 1.31 [s, 6H, 2-$(CH_3)_2$]. Ref., Neumann, W. P.; Hillgartner, H. *Synthesis*, 537 (1971).

EXAMPLE 23

(R/S)-1,2,3,4-Tetrahydro-2,2,4,10-tetramethyl-6-trifluoromethyl-9-pyrido[3,2-g]quinoline (Compound 123. Structure 5 of Scheme II, where $R^1=R^3=R^4=R^5=$Me, $R^2=R^6=$H). This compound was prepared from 8-bromo-1,2,3,4-tetrahydro-2,2,4,10-tetramethyl-6-trifluoromethyl-8-pyridono[5,6-g]quinoline (80 mg, 0.21 mmol) in the manner previously described for Compound 122 to give 60 mg (64%) of the desired product as a yellow solid. Data for Compound 123: $^1$H NMR (400 MHz, $CDCl_3$) 8.81 (d, 1H, J=4.4, 8-H), 7.81 (br s, 1H, 5-H), 7.31 (d, 1H, J=4.4, 7-H), 4.13 [br s, 1H, $(CH_3)_2CNH$], 3.14 (m, 1H, 4-H), 2.55 (s, 3H, 10-$CH_3$), 1.88 and 1.55 [dd of Abq, 2H, $J_{AB}$=12.9, $J_A$=5.1, 1.5 (3-$H_{eq}$), $J_B$=12.9, 0 (3-$H_{ax}$)], 1.49 (d, 3H, J=6.7, 4-$CH_3$), 1.39 and 1.30 [2s, 2×3H, 2-$(CH_3)_2$].

EXAMPLE 24

1,2,3,4-Tetrahydro-1,2,2-trimethyl-6-trifluoromethyl-9-pyrido[3,2-g]quinoline (Compound 124, Structure 22 of Scheme VI, where $R^1=R^5=R^6=H$, $R^3=R^4=Me$, X=H). This compound was prepared from 1,2,3,4-Tetrahydro-2,2-trimethyl-6-trifluoromethyl-9-pyrido[3,2-g]quinoline (10 mg, 36 μmol) in the manner previously described for Compound 102, affording 8 mg (76%) of Compound 124 as a fluorescent yellow-orange solid. Data for Compound 124: $^1$H NMR (400 MHz, CDCl$_3$) 8.74 (d, 1H, J=4.5, 8-H), 7.63 (s, 1H, 5-H), 7.29 (d, 1H, J=4.5, 7-H), 7.10 (s, 1H, 10-H), 2.98 (s, 3H, NCH$_3$), 2.95 (t, 2H, J=6.5, 4-H), 1.89 (t, 2H, J=6.5, 3-H), 1.33 [s, 6H, 2-(CH$_3$)$_2$].

EXAMPLE 25

(R/S)-4-Ethyl-1,2,3,4-tetrahydro-6-trifluoromethyl-9-pyrido[3,2-g]quinoline (Compound 125. Structure 5 of Scheme II, where $R^1=R^2=R^3=R^4=R^6=H$, $R^5=Et$). This compound was prepared from Compound 121(100 mg, 254 μmol) in the manner previously described for Compound 122, affording 49 mg (63%) of Compound 125 as a fluorescent yellow solid. Data for Compound 125: $^1$H NMR (400 MHz, CDCl$_3$) 8.73 (d, 1H, J=4.6, 8-H), 7.69 (s, 1H, 5-H), 7.28 (d, 1H, J=4.6, 7-H), 7.04 (s, 1H, 10-H), 4.59 (br s, 1H, NH), 3.44 (m, 2H, 2-H), 2.90 (m, 1H, 4-H), 1.98 (m, 2H, 3-H), 1.72 (m, 2H, 4-CH$_2$CH$_3$), 1.03 (t, 3H, J=7.4, 4-CH$_2$CH$_3$).

EXAMPLE 26

7-Fluoro-1,2,3,4-tetrahydro-2,2-dimethyl-6-trifluoromethyl-9-pyrido[3,2-g]quinoline (Compound 126, Structure 5 of Scheme II, where $R^1=R^2=R^5=H$, $R^3=R^4=Me$, $R^6=F$). This compound was prepared from 8-bromo-7-fluoro-1,2,3,4-tetrahydro-2,2-dimethyl-6-trifluoromethyl-9-pyrido[3,2-g]quinoline (202 mg, 0.540 mmol) in the manner previously described for Compound 122, affording 127 mg (79%) of Compound 126 as a fluorescent yellow solid. Data for Compound 126: $^1$H NMR (400 MHz, CDCl$_3$) 8.39 (s, 1H, 8-H), 7.64 (s, 1H, 5-H), 6.98 (s, 1H, 10-H), 4.31 (br s, 1H, NH), 3.01 (t, 2H, J=6.2, 4-H), 1.81 (t, 2H, J=6.7, 3-H), 1.31 [s, 6H, 2-(CH$_3$)$_2$].

EXAMPLE 27

8-Cyano-1,2,3,4-tetrahydro-2,2-dimethyl-6-trifluoromethyl-9-pyrido[3,2-g]quinoline (Compound 127, Structure 6 of Scheme II, where $R^1=R^2=R^5=R^6=H$, $R^3=R^4=Me$). General Procedure for the Preparation of 8–Cyano-Derivatives. To a 10 mL r.b. flask containing 1,2,3,4-tetrahydro-2,2-dimethyl-6-trifluoromethyl-9-pyrido[3,2-g] quinoline (500 mg, 1.78 mmol) suspended in CH$_2$Cl$_2$ (5 mL) at room temperature was added potassium cyanide (349 mg, 5.36 mmol) dissolved in water (1 mL) in one portion. Then p-toluenesulfonyl chloride (713 mg, 3.57 mmol) dissolved in CH$_2$Cl$_2$ (4 mL) was added to the reaction mixture slowly over 30 min. The flask was then sealed and stirred for 5 d. The reaction mixture was then filtered through a pad of Celite and washed with CH$_2$Cl$_2$. The filtrate was concentrated under reduced pressure. Purification by flash column chromatography (silica gel, hexanes/EtOAc, 2:1) followed by recrystallization from hot MeOH afforded 343 mg (63%) of cyanoquinoline 127 as bright orange needles. Data for Compound 127: $^1$H NMR (400 MHz, CDCl$_3$) 7.75 (s, 1H, 5-H), 7.54 (s, 1H, 7-H), 7.03 (s, 1H, 10-H), 4.59 (br s, 1H, NH), 3.06 (t, 2H, J=6.3, 4-H), 1.83 (t, 2H, J=6.7, 3-H), 1.33 [s, 6H, 2-(CH$_3$)$_2$]. Ref., Boger, et al., *J. Org. Chem.* 49:4056–4058 (1984).

EXAMPLE 28

8-Cyano-1,2,3,4-tetrahydro-1,2,2-dimethyl-6-trifluoromethyl-9-pyrido [3,2-g]quinoline (Compound 128, Structure 22 of Scheme VI, where $R^1=R^5=R^6=H$, $R^3=R^4=Me$, X=CN). This compound was prepared from Compound 127 (23 mg, 75 μmol) in the manner previously described for Compound 102, affording 15 mg (63%) of Compound 128 as a fluorescent yellow-orange solid. Data for Compound 128: $^1$H NMR (400 MHz, CDCl$_3$) 7.66 (s, 1H, 5-H), 7.55 (s, 1H, 7-H), 7.06 (s, 1H, 10-H), 3.00 (s, 3H, NCH$_3$), 2.99 (t, 2H, J=6.1, 4-H), 1.91 (t, 2H, J=6.5, 3-H), 1.36 [s, 6H, 2-(CH$_3$)$_2$].

EXAMPLE 29

(R/S)-8-Cyano-4-ethyl-1,2,3,4-tetrahydro-6-trifluoromethyl-9-pyrido[3,2-g]quinoline (Compound 129. Structure 6 of Scheme II, where $R^1=R^2=R^3=R^4=R^6=H$, $R^5=Et$). This compound was prepared from 8–Cyano-4-ethyl-1,2,3,4-tetrahydro-6-trifluoromethyl-9-pyrido[3,2-g] quinoline (44 mg, 155 μmol) in the manner previously described for Compound 127, affording 22 mg (46%) of Compound 129 as a fluorescent yellow-orange solid. Data for Compound 129: $^1$H NMR (400 MHz, CDCl$_3$) 7.72 (s, 1H, 5-H), 7.54 (s, 1H, 7-H), 7.05 (s, 1H, 10-H), 4.81 (br s, 1H, NH), 3.48 (m, 2H, 2-H), 2.92 (m, 1H, 4-H), 2.00 (m, 2H, 3-H), 1.72 (m, 2H, 4-CH$_2$CH$_3$), 1.03 (t, 3H, J=7.4, 4-CH$_2$CH$_3$).

EXAMPLE 30

(R/S)-8-Cyano-4-ethyl-1,2,3,4-tetrahydro-1-methyl-6-trifluoromethyl-9-pyrido[3,2-g]quinoline (Compound 130, Structure 22 of Scheme VI, where $R^1=R^3=R^4=R^6=H$ $R^5=Et$, X=CN). This compound was prepared from (R/S)-8-cyano-4-ethyl-1,2,3,4-tetrahydro-6-trifluoromethyl-9-pyrido[3,2-g]quinoline (5.0 mg, 16 μmol) in the manner previously described for Compound 102, affording 1.9 mg (36%) of Compound 130 as a fluorescent yellow-orange solid. Data for Compound 130: $^1$H NMR (400 MHz, CDCl$_3$) 7.66 (s, 1H, 5-H), 7.55 (s, 1H, 7-H), 7.06 (s, 1H, 10-H), 3.48 & 3.56 (2m, 2H, 2-H), 3.09 (s, 3H, J=7.4, NCH$_3$), 2.90 (m, 1H, 4-H), 1.99 (m, 2H, 3-H), 1.68 (m, 2H, 4-CH$_2$CH$_3$), 1.03 (t, 3H, J=7.4, 4-CH$_2$CH$_3$).

EXAMPLE 31

(R/S)-9-Benzoyl-8-cyano-1,2,3,4,8,9-hexahydro-2,2-dimethyl-6-trifluoromethyl-9-pyrido[3,2-g]quinoline (Compound 131, Structure 8 of Scheme II, where $R^1=R^2=R^5=R^6=R^7=H$, $R^3=R^4=Me$). To a 5 mL r.b. flask, 1,2,3,4-Tetrahydro-2,2-dimethyl-6-trifluoromethyl-9-pyrido[3,2-g]quinoline (Compound 122) (100 mg, 357 μmol) dissolved in CH$_2$Cl$_2$ (1 mL) was added potassium cyanide (70 mg, 1.07 mmol) dissolved in H$_2$O (0.5 mL) in one portion. Benzoyl chloride (7, where $R^7=H$) (83 μg, 714 μmol) dissolved in CH$_2$Cl$_2$ (1 mL) was then added to the reaction mixture slowly over 50 min, and the mixture was stirred at room temperature for 3.5 h. The reaction mixture was quenched with saturated NaHCO$_3$ and extracted with CH$_2$Cl$_2$ (3×5 mL). The combined organic layers were dried ($Na_2SO_4$) and concentrated under reduced pressure. Purification by flash column chromatography (silica gel, hexanes/EtOAc, 2:1) afforded 65 mg (44%) of dihydropyridine 131 as a pale yellow solid. Data for Compound 131: $^1$H NMR (400 MHz, $CDCl_3$) 7.45 (t, 1H, J=6.5, 4'-H), 7.38 (d, 2H, J=7.1, 2'-H), 7.33 (t, 2H, J=7.5, 3'-H ), 7.14 (s, 1H, 5-H), 6.31 & 6.27 (ABq, 2H, $J_{AB}$=6.8, 7,8-H), 5.70 (s, 1H, 10-H), 3.61 (br s, 1H, NH), 2.73 (t, 2H, J=6.7, 4-H), 1.64 (t, 2H, J=6.7, 3-H), 1.12 & 1.09 [2s, 2×3H, 2-$(CH_3)_2$]. Ref., Popp, F. D., et al., *J. Org. Chem.*, 26:4930–4932 (1961).

EXAMPLE 32

(R/S)-8-Cyano-1,2,3,4,8,9-hexahydro-2,2-dimethyl-9-p-toluoyl-6-trifluoromethyl-9-pyrido[3,2-g]quinoline (Compound 132, Structure 8 of Scheme II, where $R^1$=$R^2$=$R^5$=$R^6$=H, $R^3$=$R^4$=$R^7$=Me). This compound was prepared from Compound 122 (100 mg, 357 μmol) in the manner previously described for Compound 131, affording 108 mg (71%) of Compound 132 as a fluorescent yellow-orange solid. Data for Compound 132: $^1$H NMR (400 MHz, $CDCl_3$) 7.30 (d, 2H, J=8.0, 2'-H), 7.13 (s, 1H, 5-H), 7.12 (d, 2H, J=8.2, 3'-H), 6.30 & 6.23 (ABq, 2H, $J_{AB}$=7.3, 7,8-H), 5.74 (s, 1H, 10-H), 3.64 (br s, 1H, NH), 2.74 (t, 2H, J=6.6, 4-H), 2.37 (s, 3H, 4'-$CH_3$), 1.65 (t, 2H, J=6.7, 3-H), 1.14 & 1.11 [2s, 2×3H, 2-$(CH_3)_2$].

EXAMPLE 33

1,2,3,4-Tetrahydro-2,2-dimethyl-6-trifluoromethyl-8-thiopyridono[5,6-g]quinoline (Compound 133, Structure 9 of Scheme III, where $R^1$=$R^2$=$R^5$=$R^6$=H, $R^3$=$R^4$=Me). General Procedure for the Preparation of 8-Sulfoxy-Derivatives. To a flame-dried 50-mL r.b. flask containing Lawesson's reagent (1.82 g, 4.50 mmol) suspended in THF (15 mL) was added 1,2,3,4-tetrahydro-2,2-dimethyl-6-trifluoromethyl-9-pyrido[3,2-g]quinoline (1.00 g, 3.18 mmol) in one portion. The reaction mixture was to allowed to stir at room temperature for 17.5 h. The reaction was then quenched with water and EtOAc. The layers were separated, and the aqueous layer was neutralized with saturated $NaHCO_3$ and extracted with EtOAc (3×30 mL). The combined organic layers were washed with water (20 mL), saturated $NaHCO_3$ (20 mL), and brine (20 mL), dried ($Na_2SO_4$), and concentrated under reduced pressure to yield a brown solid. Purification by flash column chromatography (silica gel, hexanes/EtOAc, 2:1) followed by recrystallization of the resultant solid from hot EtOAc afforded 617 mg (80%) of the thioquinolone 133 as orange needles. Data for Compound 133: $^1$H NMR (400 MHz, $CDCl_3$) 11.32 (br s, 1H, CSNH), 7.44 (s, 1H, 5-H), 7.39 (s, 1H, 7-H), 6.45 (s, 1H, 10-H), 4.58 (br s, 1H, NH), 2.87 (t, 2H, J=6.6, 4-H), 1.76 (t, 2H, J=6.7, 3-H), 1.28 [s, 6H, 2-$(CH_3)_2$].

1,2,3,4-Tetrahydro-2,2-dimethyl-8-methylthio-6-trifluoromethyl-9-pyrido[3,2-g]quinoline (Compound 134, Structure 10 of Scheme III, where $R^1$=$R^2$=$R^5$=$R^6$=H, $R^3$=$R^4$=$R^8$=Me). To a flame-dried 50-mL r.b. flask containing thioquinolone 133 (1.82 g, 4.50 mmol) dissolved in DMF (7 mL) was added methyl iodide (285 μL, 4.54 mmol) dropwise over 5 min. The reaction mixture was to allowed to stir at room temperature for 14 h. The reaction was then quenched with water and EtOAc. The layers were separated, and the aqueous layer was extracted with EtOAc (3×20 mL). The combined organic layers were washed with water (20 mL), and brine (20 mL), dried ($Na_2SO_4$), and concentrated under reduced pressure to yield a orange solid. Purification by flash column chromatography (silica gel, hexanes/EtOAc, 1:1) afforded 469 mg (90%) of the methylthioquinoline 134 as a yellow solid. Data for Compound 134: $^1$H NMR (400 MHz, $CDCl_3$) 7.59 (s, 1H, 5-H), 7.15 (s, 1H, 7-H), 6.91 (s, 1H, 10-H), 4.25 (br s, 1H, NH), 2.98 (t, 2H, J=6.7, 4-H), 2.66 (s, 3H, $SCH_3$), 1.80 (t, 2H, J=6.7, 3-H), 1.29 [s, 6H, 2-$(CH_3)_2$].

(R/S)-1,2,3,4-Tetrahydro-2,2-dimethyl-8-methylsulfinyl-6-trifluoromethyl-9-tpyrido[3,2-g]quinoline (Compound 135. Structure 11 of Scheme III, where $R^1$=$R^2$=$R^5$=$R^6$=H, $R^3$=$R^4$=$R^8$=Me). To a 5-mL r.b. flask containing methylthioquinoline 134 (50.0 mg, 145 μmol) dissolved in EtOH (1 mL) was added monoperoxyphthalic acid, magnesium salt hexahydrate (MMPP, 54.0 mg, 87.0 μmol, 80%) dissolved in EtOH (350 μL) in one portion. The reaction mixture was heated to reflux and stirred for 1 h. The reaction was then quenched with saturated $NaHCO_3$ and extracted with $CH_2Cl_2$ (3×10 mL). The combined organic layers were washed with water (10 mL), dried ($Na_2SO_4$), and concentrated under reduced pressure to yield a brown solid. Purification by preparative thin layer chromatography (silica gel, hexanes/EtOAc, 1:1) afforded 46 mg (92%) of the sulfoxide 135 as a yellow solid. Data for Compound 135: $^1$H NMR (400 MHz, $CDCl_3$) 8.00 (s, 1H, 7-H), 7.78 (s, 1H, 5-H), 6.96 (s, 1H, 10-H), 4.48 (br s, 1H, NH), 3.06 (t, 2H, J=6.7, 4-H), 2.90 (s, 3H, $SOCH_3$), 1.83 (t, 2H, J=6.6, 3-H), 1.33 (s, 3H, 2-$(CH_3)$ cis), 1.32 [s, 3H, 2-$(CH_3)$trans]. Ref., Brougham, P.; et al., *Synthesis*, 1015–1017 (1987).

EXAMPLE 34

1,2,3,4-Tetrahydro-2,2-dimethyl-8-methylsulfonyl-6-trifluoromethyl-9-pyrido[3,2-g]guinoline (Compound 136, Structure 12 of Scheme III, where $R^1$=$R^2$=$R^5$=$R^6$=H, $R^3R^4$=$R^8$=Me). To a 5-mL r.b. flask containing the methylthioquinoline 134 (50.0 mg, 145 pmol) dissolved in $CH_2Cl_2$ (1 mL) at −78° C. was added 3-chloroperoxybenzoic acid (92.0 mg, 319 μmol, ca. 60%) dissolved in $CH_2Cl_2$ (1 mL) dropwise over 10 min. The reaction mixture was stirred for 20 min at −78 ° C. The reaction was then quenched with 1:1 solution of saturated $NaHCO_3$ and 10% $NaHSO_3$, and extracted with $CH_2Cl_2$ (3×5 mL). The combined organic layers were washed with water (10 mL), dried ($Na_2SO_4$), and concentrated under reduced pressure e to yield a brown-orange solid. Purification by preparative thin layer chromatography (silica gel, hexanes/EtOAc, 1:2) afforded 24 mg (49%) of the sulfoxide 135 as a yellow solid and 3 mg (3%) of the sulfone 136 as a yellow foam. Data for Compound 136: $^1$H NMR (400 MHz, $CDCl_3$) 7.97 (s, 1H, 7-H), 7.78 (s, 1H, 5-H), 7.07 (s, 1H, 10-H), 4.57 (br s, 1H, NH), 3.31 (s, 3H, $SOCH_3$), 3.07 (t, 2H, J=6.7, 4-H), 1.84 (t, 2H, J=6.7, 3-H), 1.33 [s, 6H, 2-$(CH_3)_2$].

EXAMPLE 35

(R/S)-7-Fluoro-1,2,3,4-tetrahydro-2,2-dimethyl-6-trifluoromethyl-8-methylsulfinyl-9-pyrido[3,2-g]quinoline (Compound 137. Structure 11 of Scheme III, where $R^1$=$R^2$=$R^5$=H, $R^3$=$R^4$=$R^8$=Me, $R^6$=F). This compound was prepared from 7-Fluoro-1,2,3,4-tetrahydro-2,2-dimethyl-6-trifluoromethyl-8-methylthio-9-pyrido[3,2-g]guinoline (210 mg, 0.61 mmol) in the manner previously described for Compound 135 affording 198 mg (90%) of the desired sulfoxide 137 as a fluorescent yellow-orange solid. Data for Compound 137: $^1$H NMR (400 MHz, CDCl$_3$) 7.75 (s, 1H, 5-H), 7.19 (s, 1H, 10-H), 4.44 (br s, 1H, NH), 3.05 (dd, 2H, J=6.3, 6.3, 3-H), 2.98 (s, 3H, S—CH$_3$), 1.82 (dd, 2H, J=6.7, 6.7,2-H), 1.32 and 1.31 [2s, 2×3H, 2-(CH$_3$)$_2$].

EXAMPLE 36

1,2,3,4-Tetrahydro-2,2-dimethyl-8-(1-n-butylthio)-6-trifluoromethyl-9-pyrido[3,2-g]guinoline (Compound 138, Structure 10 of Scheme III, where $R^1=R^2=R^5=R^6=H$, $R^3=R^4=$Me, $R^8=$n-Bu). This compound was prepared from Compound 133 (100 mg, 302 μmol) in the manner previously described for Compound 134, with the exception that the reaction was heated at 80 C for 3 h, affording 115 mg (97%) of Compound 138 as a fluorescent yellow-orange solid. Data for Compound 138: $^1$H NMR (400 MHz, CDCl$_3$) 7.58 (s, 1H, 5-H), 7.12 (s, 1H, 7-H), 6.89 (s, 1H, 10-H), 4.24 (br s, 1H, NH), 3.28 (t, 2H, J=7.3, SCH$_2$), 2.97 (t, 2H, J=6.8, 4-H), 1.79 (t, 2H, J=6.7, 3-H), 1.73 (p, J=7.4, 2H, 2'-H), 1.49 (h, J=7.4, 3'-H), 1.28 [s, 6H, 2-(CH$_3$)$_2$], 0.97 (t, J=7.3, 4'-H).

(R/S)-1,2,3,4-Tetrahydro-2,2-dimethyl-8-(1-n-butylsulfinyl)-6-trifluoromethyl-9-pyrido[3,2-g]quinoline (Compound 139, Structure 11 of Scheme III, where $R^1=R^2=R^5=R^6=H$, $R^3=R^4=$Me, $R^8=$n-Bu). This compound was prepared from Compound 138 (103 mg, 655 μmol) in the manner previously described for Compound 135, affording 71 mg (68%) of Compound 139 as a red oil. Data for Compound 139: $^1$H NMR (400 MHz, CDCl$_3$) 7.97 (s, 1H, 5-H), 7.77 (s, 1H, 7-H), 6.96 (s, 1H, 10-H), 4.47 (br s, 1H, NH), 3.12 & 2.96 (2m, 2H, SOCH$_2$), 3.05 (t, 2H, J=6.8, 4-H), 1.83 (t, 2H, J=6.7, 3-H), 1.89 & 1.50 (2m, 2H, 2'-H), 1.43 (m, 2H, 3'-H), 1.33 & 1.32 [2s, 6H, 2-(CH$_3$)$_2$], 0.92 (t, J=7.3, 4'-H).

EXAMPLE 37

1,2,3,4-Tetrahydro-2,2-dimethyl-8-(2,2,2-trifluoroethyl-1-thio)-6-trifluoromethyl-9-pyrido[3,2-g]quinoline (Compound 140, Structure 10 of Scheme III, where $R^1=R^2=R^5=R^6=H$, $R^3=R^4=$Me, $R^8=$CH$_2$CF$_3$). This compound was prepared from Compound 133 (100 mg, 302 μmol) in the manner previously described for Compound 134, affording 50 mg (45%) of Compound 140 as a fluorescent yellow-orange solid. Data for Compound 140: $^1$H NMR (400 MHz, CDCl$_3$) 7.61 (s, 1H, 5-H), 7.14 (s, 1H, 7-H), 6.90 (s, 1H, 10-H), 4.32 (br s, 1H, NH), 4.17 (q, 2H, J=10.0, SCH$_2$), 2.98 (t, 2H, J=6.8, 4-H), 1.78 (t, 2H, J=6.7, 3-H), 1.28 [s, 6H, 2-(CH$_3$)$_2$].

EXAMPLE 38

(R/S)-4-Ethyl-1,2,3,4-tetrahydro-6-trifluoromethyl-8-thiopyridono[5,6-g]quinoline (Compound 141, Structure 9 of Scheme III, where $R^1=R^2=R^3=R^4=R^6=H$, $R^5=$Et). This compound was prepared from 4-Ethyl-1,2,3,4-tetrahydro-6-trifluoromethyl-8-pyridono[5,6-g]quinoline (250 mg, 795 μmol) in the manner previously described for Compound 133, affording 255 mg (97%) of Compound 141 as a fluorescent yellow-orange solid. Data for Compound 141: $^1$H NMR (400 MHz, d$_6$-DMSO) 7.32 (br s, 1H, CSNH), 7.24 (s, 1H, 5-H), 7.02 (s, 1H, 7-H), 6.64 (s, 1H, 10-H), 3.26 (m, 2H, 2-H), 2.70 (m, 1H, 4-H), 1.76 (m, 2H, 3-H), 1.53 (m, 2H, 4-CH$_2$CH$_3$), 0.93 (t, 3H, J=7.4, 4-CH$_2$CH$_3$).

(R/S)-4-Ethyl-1,2,3,4-tetrahydro-8-methylthio-6-trifluoromethyl-9-pyrido[3,2-g]quinoline (Compound 142, Structure 10 of Scheme III, where $R^1=R^2=R^3=R^4=R^6=H$, $R^5=$Et, $R^8=$Me). This compound was prepared from Compound 141 (180 mg, 302 μmol) in the manner previously described for Compound 134, affording 84 mg (80%) of Compound 142 as a fluorescent yellow-orange solid. Data for Compound 142: $^1$H NMR (400 MHz, CDCl$_3$) 7.57 (s, 1H, 5-H), 7.14 (s, 1H, 7-H), 6.91 (s, 1H, 10-H), 4.49 (br s, 1H, NH), 3.42 (m, 2H, 2-H), 2.84 (m, 1H, 4-H), 2.65 (s, 3H, SCH$_3$), 1.95 (m, 2H, 3-H), 1.70 (m, 2H, 4-CH$_2$CH$_3$), 1.02 (t, 3H, J=7.4, 4-CH$_2$CH$_3$).

(R/S)-4-Ethyl-1,2,3,4-tetrahydro-8-methylsulfinyl-6-trifluoromethyl-9-pyrido[3.2-g]guinoline (Compound 143, Structure 11 of Scheme III, where $R^1=R^2=R^3=R^4=R^6=H$, $R^5=$Et, $R^8=$Me). This compound was prepared from Compound 141 (69 mg, 200 μmol) in the manner previously described for Compound 135 affording 53 mg (73%) of Compound 143 as a fluorescent yellow-orange solid. Data for Compound 143: $^1$H NMR (400 MHz, CDCl$_3$) 7.99 & 8.00 (2s, 1H, 7-H), 7.75 (s, 1H, 5-H), 6.98 (s, 1H, 10-H), 4.71 (br s, 1H, NH), 3.48 (m, 2H, 2-H), 2.92 (m, 1H, 4-H), 2.89 & 2.90 (2s, 3H, SOCH$_3$), 2.01 (m, 2H, 3-H), 1.71 (m, 2H, 4-CH$_2$CH$_3$), 1.04 (t, 3H, J=7.3, 4-CH$_2$CH$_3$).

EXAMPLE 39

1,2,3,4-Tetrahydro-8-(4'-methoxybenzylamino)-2,2-dimethyl-6-trifluoromethyl-9-pyrido[3,2-g]guinoline (Compound 144, Structure 13 of Scheme IV, where $R^1=R^2=R^5=R^6=H$, $R^3=R^4=$Me, $R^9=$p-MeOPhCH). To a flame-dried 10-mL r.b. flask containing 1,2,3,4-tetrahydro-2,2-dimethyl-6-trifluoromethyl-9-pyrido[3,2-g]quinoline (1.25 g, 3.97 mmol),p-toluenesulfonic acid monohydrate (76 mg, 0.40 mmol), p-methoxybenzylamine (1.56 mL, 11.9 mmol), and 1,1,1,3,3,3-hexamethyldisilizane (1.26 mL, 5.96 mmol) was heated to 140° C. for 2 h and then at 160° C. with distillation of hexamethyldisiloxane. The reaction mixture was allowed to cool to room temperature and was added CH$_2$Cl$_2$ (5 mL) and 0.5 M NaOH (3 mL). The layers were separated, and the aqueous phase was diluted with water (10 mL) and extracted with CH$_2$Cl$_2$ (3×10 mL). The combined organic layers were washed with brine (20 mL), dried (Na$_2$SO$_4$), and concentrated under reduced pressure to yield a brown solid. Purification by flash column chromatography (silica gel, hexanes/EtOAc, 1:1) afforded 1.12 g (65 %) of aminoquinoline 144 as a yellow solid. Data for Compound 144: $^1$H NMR (400 MHz, CDCl$_3$) 7.47 (s, 1H, 5-H), 7.30 (d, 2H, J=8.7, 2'-H), 6.86 (d, 2H, J=8.6, 3'-H), 6.68 (s, 1H, 10-H), 6.58 (s, 1H, 7-H), 4.95 (br s, 1H, 8-NH), 4.59 (d, 2H, J=5.5, ArCH$_2$N), 4.12 (br s, 1H, 1-NH), 3.79 (s, 3H, OCH$_2$), 2.92 (t, 2H, J=6.7, 4-H), 1.76 (t, 2H, J=6.7, 3-H), 1.26 [s, 6H, 2-(CH$_3$)$_2$]. Ref Vorbruggen, H., et al., *Chem. Ber.*, 117:1523–1541 (1984).

8-Amino-1,2,3,4-tetrahydro-2,2-dimethyl-6-trifluoromethyl-9-pyrido[3,2-g]quinoline (Compound 145, Structure 14 of Scheme IV, where $R^1=R^2=R^5=R^6=H$, $R^3=R^4=Me$). To a 5-mL r.b. flask containing 1,2,3,4-Tetrahydro-8-(4'-methoxybenzylamino)-2,2-dimethyl-6-trifluoromethyl-9-pyrido[3,2-g]quinoline (Compound 144) (100 mg, 241 μmol) dissolved in trifluoroacetic acid (2 mL) was heated to 65° C. and stirred for 3 h. The reaction was cooled to room temperature, quenched with ice and saturated $NaHCO_3$, and extracted with EtOAc (3×10 mL). The combined organic layers were washed with brine (10 mL), dried ($Na_2SO_4$), and concentrated under reduced pressure to yield a waxy yellow solid. Purification by flash column chromatography (silica gel, EtOAc) afforded 45 mg (62%) of the aminoquinoline 145 as a yellow solid. Data for Compound 145: $^1$H NMR (400 MHz, $CDCl_3$) 7.50 (s, 1H, 5-H), 6.67 (s, 1H, 10-H), 6.62 (s, 1H, 7-H), 4.68 (br s, 2H, 8-$NH_2$), 4.17 (br s, 1H, NH), 2.93 (t, 2H, J=6.7, 4-H), 1.77 (t, 2H, J=6.7, 3-H), 1.27 [s, 3H, 2-$(CH_3)_2$]. Ref., Buckle, D. R., et al., *J. Chem. Soc., Perkin Trans. I*, 627 (1982).

1,2,3,4-Tetrahydro-8-methanesulfonamido-2,2-dimethyl-6-trifluoro-methyl-9-pyrido[3,2-g]quinoline (Compound 146, Structure 16 of Scheme IV, where $R^1=R^2=R^5=R^6=H$, $R^3=R^4=R^{10}=Me$) and 1,2,3,4-Tetrahydro-8-bis(methanesulfon)amido-2,2-dimethyl-6-trifluoromethyl-9-pyrido[3,2-g]quinoline (Compound 147, Structure 17 of Scheme IV, where $R^1=R^2=R^5=R^6=H$, $R^3=R^4=R^{10}=Me$). To a 5-mL r.b. flask containing 8-amino-1,2,3,4-tetrahydro-2,2-dimethyl-6-trifluoromethyl-9-pyrido[3,2-g]quinoline (50 mg, 170 μmol) and triethylamine (47 μL, 340 μmol) dissolved in $CH_2Cl_2$ (1 mL) at 0° C. was added methanesufonyl chloride (20 μL, 254 μmol) and DMAP (approx. 1 mg). The reaction mixture was stirred for 15 min at 0° C. The reaction was then quenched with pH 7.0 buffer (3 ml) and extracted with EtOAc (3×5 mL). The combined organic layers were washed with brine (10 mL), dried ($Na_2SO_4$), and concentrated under reduced pressure to yield a brown solid. Purification by preparative thin layer chromatography (silica gel, hexanes/EtOAc, 1:2) afforded 6.4 mg (10%) of the sulfonamide 146 as a yellow solid and 4.4 mg (6%) of the bissulfonamide 147 as a yellow foam. Data for Compound 146: $^1$H NMR (400 MHz, $CDCl_3$) 11.00 (br s, 1H, $CH_3SO_2NH$), 7.42 (s, 1H, 5-H), 6.75 (s, 1H, 10-H), 6.28 (s, 11H, 7-H), 4.53 (br s, 1H, NH), 3.09 (s, 3H, $SO_2CH_3$), 2.88 (t, 2H, J=6.5, 4-H), 1.76 (t, 2H, J=6.6, 3-H), 1.29 [s, 6H, 2-$C(CH_3)_2$]. Data for Compound 147: $^1$H NMR (400 MHz, $CDCl_3$) 7.73 (s, 1H, 5-H), 7.21 (s, 1H, 7-H), 6.97 (s, 1H, 10-H), 4.44 (br s, 1H, NH), 3.64 (s, 6H, $SO_2CH_3$), 3.04 (t, 2H, J=6.4, 4-H), 1.81 (t, 2H, J=6.7, 3-H), 1.30 [s, 6H, 2-$C(CH_3)_2$].

EXAMPLE 40

1,2,3,4-Tetrahydro-2,2-dimethyl-6,8-di(trifluoromethyl)-9-pyrido[3,2-g]quinoline (Compound 148, Structure 20 of Scheme V, where $R^1=R^2=R^5=R^6=H$, $R^3=R^4=Me$). In a 25-mL r.b. flask, a solution of 7-amino-1,2,3,4-tetrahydro-2,2-dimethylquinoline (Compound 19) (201 mg) in toluene (6 mL) was treated with 1,1,1,5,5,5-hexafluoroacetylacetone (0.18 mL) and stirred at room temperature for 15 min. The reaction mixture turned cloudy and was treated with p-toluenesulfonic acid hydrate (10 mg). The reaction mixture was stirred 15 min at room temperature and $K_2CO_3$ (0.5 g) added. The reaction mixture was stirred vigorously for 5 min, filtered, and concentrated to a yellow oil. Purification by silica gel chromatography (hexane:EtOAc, 12:1 to 8:1 gradient) afforded 0.34 g (86%) of Compound 148 as a yellow powder. Data for Compound 148: $^1$H NMR (400 MHz, $CDCl_3$) 7.76 (s, 1H, 5-H), 7.58 (s, 1H, 7-H), 7.09 (s, 1H, 10-H), 4.47 (br exch s, 1H, NH), 3.06 (t, J=6.6, 2H, 4-H), 1.83 (t, J=6.6, 2H, 3-H), 1.32 [s, 6H, 2-$C(CH_3)_2$]; TLC $R_f$=0.62 (hexane:EtOAc, 3:1).

EXAMPLE 41

(R/S)-4-Ethyl-1,2,3,4-tetrahydro-6,8-di(trifluoromethyl)-9-pyrido[3,2-g]quinoline (Compound 149, Structure 20 of Scheme V, where $R^1=R^2=R^3==R^4=R^6=H$, $R^5=Et$). In a 25-mL r.b. flask, a solution of 7-amino-4-ethyl-1,2,3,4-tetrahydroquinoline (120 mg) in toluene (15 mL) was treated with 1,1,1,5,5,5-hexafluoroacetylacetone (0.20 g) and stirred at room temperature for 15 min. The reaction mixture turned cloudy and was treated with p-toluenesulfonic acid hydrate (10 mg). The reaction mixture was stirred 15 min at room temperature and $K_2CO_3$ (0.5 g) added. The reaction mixture was stirred vigorously for 5 min, filtered, and concentrated to a yellow oil. Purification by silica gel chromatography (hexane:EtOAc, 8:1) afforded 144 mg (61%) of Compound 149 as a yellow powder. Data for Compound 149: $^1$H NMR (400 MHz, $CDCl_3$) 7.74 (s, 1H, 5-H), 7.58 (s, 1H, 7-H), 7.12 (s, 1H, 10-H), 4.73 (br exch s, 1H, NH), 3.48 (m, 2H), 2.92 (m, 1H), 1.98 (m, 2H), 1.76 (m, 1H), 1.68 (m, 1H), 1.03 (t, 3H, J=7.4, 4-$CH_2CH_3$).

EXAMPLE 42

Steroid Receptor Activity

Utilizing the "cis-trans" or "co-transfection" assay described in U.S. Pat. Nos. 4,981,784 and 5,071,773, the disclosures of which are incorporated herein by reference, the compounds of the present invention were tested and found to have strong, specific activity as both agonists, partial agonists and antagonists of AR. The co-transfection assay is also described by Evans et al., *Science*, 240:889–95 (May 13, 1988).

The co-transfection assay provides a method for identifying functional agonists and partial agonists which mimic, or antagonists which inhibit, the effect of native hormones, and quantifying their activity for responsive IR proteins. In this regard, the co-transfection assay mimics an in vivo system in the laboratory. Importantly, activity in the co-transfection assay correlates very well with known in vivo activity, such that the co-transfection assay functions as a qualitative and quantitative predictor of a tested compounds in vivo pharmacology. See, e.g., T. Berger et al. 41 *J. Steroid Biochem. Molec. Biol.* 773 (1992).

In the co-transfection assay, a cloned cDNA for an IR (e.g., human PR, AR or GR) under the control of a constitutive promoter (e.g., the SV 40 promoter) is introduced by transfection (a procedure to induce cells to take up foreign genes) into a background cell substantially devoid of endogenous IRs. This introduced gene directs the recipient cells to make the IR protein of interest. A second gene is also introduced (co-transfected) into the same cells in conjunction with the IR gene. This second gene, comprising the cDNA for a reporter protein, such as firefly luciferase (LUC), controlled by an appropriate hormone responsive promoter containing a hormone response element (HRE). This reporter plasmid functions as a reporter for the transcription-modulating activity of the target IR. Thus, the reporter acts as a surrogate for the products (mRNA then protein) normally expressed by a gene under control of the target receptor and its native hormone.

The co-transfection assay can detect small molecule agonists or antagonists of target IRs. Exposing the transfected cells to an agonist ligand compound increases reporter activity in the transfected cells. This activity can be conveniently measured, e.g., by increasing luciferase production, which reflects compound-dependent, IR-mediated increases in reporter transcription. To detect antagonists, the co-transfection assay is carried out in the presence of a constant concentration of an agonist to the target IR (e.g., progesterone for PR) known to induce a defined reporter signal. Increasing concentrations of a suspected antagonist will decrease the reporter signal (e.g., luciferase production). The co-transfection assay is therefore useful to detect both agonists and antagonists of specific IRs. Furthermore, it determines not only whether a compound interacts with a particular IR, but whether this interaction mimics (agonizes) or blocks (antagonizes) the effects of the native regulatory molecules on target gene expression, as well as the specificity and strength of this interaction.

The activity of selected steroid receptor modulator compounds of the present invention were evaluated utilizing the co-transfection assay, and in standard IR binding assays, according to the following illustrative Examples.

Co-Transfection Assay

CV-1 cells (African green monkey kidney fibroblasts) were cultured in the presence of Dulbecco's Modified Eagle Medium (DMEM) supplemented with 10% charcoal resin-stripped fetal bovine serum then transferred to 96-well microtiter plates one day prior to transfection.

To determine AR agonist and antagonist activity of the compounds of the present invention, the CV-1 cells were transiently transfected by calcium phosphate coprecipitation according to the procedure of Berger et al., 41 *J. Steroid Biochem. Mol. Biol.*, 733 (1992) with the following plasmids: pShAR (5 ng/well), MTV-LUC reporter (100 ng/well), pRS-β-Gal (50 ng/well) and filler DNA (pGEM; 45 ng/well). The receptor plasmid, pRShAR, contains the human AR under constitutive control of the SV-40 promoter, as more fully described in J. A. Simental et al., *J. Biol. Chem.*, 266:510 (1991).

The reporter plasmid, MTV-LUC, contains the cDNA for firefly luciferase (LUC) under control of themouse mammary tumor virus (MTV) long terminal repeat, a conditional promoter containing an androgen response element. See e.g., Berger et al. supra. In addition, pRS-β-Gal, coding for constitutive expression of *E. coli* β-galactosidase (β-Gal), was included as an internal control for evaluation of transfection efficiency and compound toxicity.

Six hours after transfection, media was removed and the cells were washed with phosphate-buffered saline (PBS). Media containing reference compounds (i.e. progesterone as a PR agonist, mifepristone ((11beta, 17beta)-11-[4-(dimethylamino) phenyl]-17-hydroxy-17-(1-propynyl)estra-4,9-dien-3-one: RU486; Roussel Uclaf) as a PR antagonist; dihydrotestosterone (DHT; Sigma Chemical) as an AR agonist and 2-OH-flutamide (the active metabolite of 2-methyl-N-[4-nitro-3-(trifluoromethyl)phenyl] pronanamide; Schering-Plough) as an AR antagonist; estradiol (Sigma) as an ER agonist and ICI 164,384 (N-butyl-3,17-dihydroxy-N-methyl-(7-alpha, 1 7-beta)-estra-1,3,5(10)-triene-7-undecanamide; ICI Americas) as an ER antagonist; dexamethasone (Sigma) as a GR agonist and RU486 as a GR antagonist; and aldosterone (Sigma) as a MR agonist and spironolactone ((7-alpha-[acetylthio]-1 7-alpha-hydroxy-3-oxopregn-4-ene-21-carboxylic acid gamma-lactone; Sigma) as an MR antagonist) and/or the modulator compounds of the present invention in concentrations ranging from $10^{-12}$ to $10^{-5}$ M were added to the cells. Three to four replicates were used for each sample. Transfections and subsequent procedures were performed on a Biomek 1000 automated laboratory work station.

After 40 hours, the cells were washed with PBS, lysed with a Triton X-100-based buffer and assayed for LUC and β-Gal activities using a luminometer or spectrophotometer, respectively. For each replicate, the normalized response (NR) was calculated as:

LUC response/B-Gal rate where β-Gal rate=β-Ga·1×$10^{-5}$/β-Gal incubation time.

The mean and standard error of the mean (SEM) of the NR were calculated. Data was plotted as the response of the compound compared to the reference compounds over the range of the dose-response curve. For agonist experiments, the effective concentration that produced 50% of the maximum response ($EC_{50}$) was quantified. Agonist efficacy was a function (%) of LUC expression relative to the maximum LUC production by the reference agonist for PR, AR, ER, GR or MR. Antagonist activity was determined by testing the amount of LUC expression in the presence of a fixed amount of DHT as an AR agonist and progesterone as a PR agonist at the $EC_{50}$ concentration. The concentration of test compound that inhibited 50% of LUC expression induced by the reference agonist was quantified ($IC_{50}$). In addition, the efficacy of antagonists was determined as a function (%) of maximal inhibition.

IR Binding Assay

AR Binding: For the whole cell binding assay, COS-1 cells in 96-well microtiter plates containing DMEM-10% FBS were transfected as described above with the following plasmid DNA: pRShAR (2 ng/well), pRS-β-Gal (50 ng/well) and pGEM (48 ng/well). Six hours after transfection, media was removed, the cells were washed with PBS and fresh media was added. The next day, the media was changed to DMEM-serum free to remove any endogenous ligand that might be complexed with the receptor in the cells.

After 24 hours in serum-free media, either a saturation analysis to determine the $K_d$ for tritiated dihydrotestosterone ($^3$H-DHT) on human AR or a competitive binding assay to evaluate the ability of test compounds to compete with $^3$H-DHT for AR was performed. For the saturation analysis, media (DMEM-0.2% CA-FBS) containing $^3$H-DHT (in concentrations ranging from 12 nM to 0.24 nM) in the absence (total binding) or presence (non-specific binding) of a 100-fold molar excess of unlabeled DHT were added to the cells. For the competitive binding assay, media containing 1 nM $^3$H-DHT and test compounds in concentrations ranging from $10^{-10}$ to $10^{-6}$ M were added to the cells. Three replicates were used for each sample. After three hours at 37° C., an aliquot of the total binding media at each concentration of $^3$H-DHT was removed to estimate the amount of free $^3$H-DHT. The remaining media was removed, the cells were washed three times with PBS to remove unbound ligand, and cells were lysed with a Triton X-100-based buffer. The lysates were assayed for amount of bound $^3$H-DHT and β-Gal activity using a scintillation counter or spectrophotometer, respectively.

For the saturation analyses, the difference between the total binding and the nonspecific binding, normalized by the β-Gal rate, was defined as specific binding. The specific binding was evaluated by Scatchard analysis to determine the $K_d$ for $^3$H-DHT. See e.g., D. Rodbard, "Mathematics and statistics of ligand assays: an illustrated guide" In: J. Langon and J. J. Clapp, eds., *Ligand Assay*, Masson Publishing U.S.A., Inc., New York, pp. 45–99, (1981). For the competition studies, the data was plotted as the amount of $^3$H-DHT (% of control in the absence of test compound) remaining over the range of the dose-response curve for a given compound. The concentration of test compound that inhibited 50% of the amount of $^3$H-DHT bound in the absence of competing ligand was quantified ($IC_{50}$) after log-logit transformation. The $K_i$ values were determined by application of the Cheng-Prusoff equation to the $IC_{50}$ values, where:

$$K_i = \frac{IC_{50}}{(1 + [^3H - DHT])/K_d \text{ for } ^3H - DHT}$$

After correcting for non-specific binding, $IC_{50}$ values were determined. The $IC_{50}$ value is defined as the concentration of competing ligand needed to reduce specific binding by 50%. The $IC_{50}$ value was determined graphically from a log-logit plot of the data. The $K_i$ values were determined by application of the Cheng-Prusoff equivuation to the $IC_{50}$ values, the labeled ligand concentration and the $K_d$ of the labeled ligand.

The agonist, antagonist and binding activity assay results of selected androgen receptor modulator compounds of present invention and the standard reference compounds on AR, as well as the cross-reactivity of selected compounds on the PR, ER, MR and GR receptors, are shown in Tables 1–2 below. Efficacy is reported as the percent maximal response observed for each compound relative to the reference agonist and antagonist compounds indicated above. Also reported in Tables 1–2 for each compound is its antagonist potency or $IC_{50}$ (which is the concentration (nM), required to reduce the maximal response by 50%), its agonist potency or $EC_{50}$ (nM).

TABLE 1

Agonist, partial agonist, antagonist and binding activity of androgen receptor modulator compounds of present invention and the reference agonist compound, dihydrotestosterone (DHT), and reference antagonists compound, 2-hydroxyflutamide (2-OH-Flut) and Casodex, on AR.

| Cmpd No. | AR Agonist CV-1 Cells | | AR Antagonist CV-1 Cells | | AR Binding |
|---|---|---|---|---|---|
| | Efficacy (%) | Potency (nM) | Efficacy (%) | Potency (nM) | KI (nM) |
| 101 | 15 ± 5 | nd | 70 ± 3 | 30 ± 9 | 320 ± 67 |
| 102 | 2 ± 3 | nd | 86 ± 2 | 336 ± 90 | >1000 |
| 103 | 16 ± 8 | nd | 60 ± 6 | 675 ± 114 | >1000 |
| 104 | 7 ± 5 | nd | 75 ± 3 | 30 ± 12 | 84 ± 22 |
| 105 | 3 | nd | 87 ± 2 | 251 ± 81 | 294 ± 289 |
| 106 | 4 ± 2 | nd | 77 ± 6 | 550 ± 15 | >1000 |
| 107 | 29 | 1035 | 61 ± 8 | 17 ± 3 | 103 |
| 108 | 36 ± 5 | 73 ± 12 | 28 ± 8 | 50 ± 27 | 81 ± 13 |
| 109 | 35 ± 12 | 89 ± 26 | 51 ± 9 | 39 ± 23 | 119 ± 65 |
| 110 | 23 ± 6 | 56 ± 17 | 56 ± 11 | 31 ± 9 | 57 |

TABLE 1-continued

Agonist, partial agonist, antagonist and binding activity of androgen receptor modulator compounds of present invention and the reference agonist compound, dihydrotestosterone (DHT), and reference antagonists compound, 2-hydroxyflutamide (2-OH-Flut) and Casodex, on AR.

| Cmpd No. | AR Agonist CV-1 Cells | | AR Antagonist CV-1 Cells | | AR Binding |
|---|---|---|---|---|---|
| | Efficacy (%) | Potency (nM) | Efficacy (%) | Potency (nM) | KI (nM) |
| 111 | 21 ± 2 | nd | 66 ± 1 | 22 ± 10 | 11 |
| 112 | 3 | nd | 86 ± 9 | 172 ± 52 | 755 |
| 113 | 12 | nd | 37 | 500 | 152 |
| 114 | 0 | nd | 68 | 1448 | >1000 |
| 115 | 0 | nd | 26 | 1136 | >1000 |
| 116 | 60 ± 4 | 37 ± 9 | 0 | nd | 5 |
| 117 | 6 | nd | 83 | 72 | 159 |
| 118 | 6 | nd | 93 | 72 | 426 |
| 119 | 6 | nd | 73 ± 7 | 47 ± 27 | 91 ± 68 |
| 120 | 5 | nd | 82 | 785 | >1000 |
| 121 | 53 ± 15 | 22 ± 14 | 8 ± 12 | nd | 55 |
| 122 | 2 | nd | 95 | 212 | 5 |
| 123 | 1 | nd | 99 | 244 | >1000 |
| 124 | 5 ± 1 | nd | 83 ± 5 | 725 ± 330 | >1000 |
| 125 | 9 ± 7 | nd | 93 ± 1 | 56 ± 17 | 93 |
| 126 | 3 ± 5 | nd | 93 ± 4 | 181 ± 73 | 58 |
| 127 | 8 ± 0 | nd | 83 ± 3 | 9 ± 2 | 22 |
| 128 | 2 ± 1 | nd | 94 ± 3 | 45 ± 8 | 86 ± 30 |
| 129 | 17 ± 1 | 42 ± 15 | 56 ± 25 | 15 ± 5 | 21 |
| 130 | 2 | nd | 89 ± 1 | 782 ± 546 | 787 |
| 131 | 0 | nd | 91 | 63 | >1000 |
| 132 | 1 | nd | 89 | 147 | 863 |
| 134 | 0 | nd | 95 | 751 | >1000 |
| 135 | 4 | nd | 98 ± 2 | 63 ± 23 | 20 |
| 136 | 10 | nd | 94 | 479 | >1000 |
| 137 | 10 | nd | 84 | 1338 | >1000 |
| 138 | 9 | nd | 75 | 1866 | >1000 |
| 139 | 5 ± 7 | nd | 96 ± 0 | 335 ± 145 | 96 |
| 140 | 7 | nd | 80 | 889 | >1000 |
| 142 | 30 ± 12 | 221 ± 108 | 60 ± 7 | 131 ± 64 | 307 |
| 143 | 37 ± 9 | 33 ± 3 | 59 | 4690 | 34 |
| 144 | 3 ± 3 | nd | 57 | 3217 | >1000 |
| 145 | 4 ± 4 | nd | 70 ± 5 | 1159 ± 280 | >1000 |
| 146 | 5 | nd | 80 | 503 | 572 |
| 147 | 4 | nd | 84 | 636 | 1231 |
| 148 | 1 ± 0 | nd | 95 ± 1 | 467 ± 11 | 2536 |
| 149 | 1 ± 0 | nd | 91 ± 1 | 117 ± 31 | 301 |
| 2-OH-Flut | 6 ± 3 | nd | 97 ± 0 | 43 ± 4 | 34 ± 8 |
| Casodex | 1 ± 0 | nd | 98 ± 0 | 338 ± 28 | 117 ± 35 |
| DHT | 100 ± 0 | 1.6 ± 0.4 | na | na | 1.7 ± 0.4 | na = not active (i.e. efficacy of <20 and potency of >10,000)
nd = not determined

TABLE 2

Overall agonist and antagonist potency of selected androgen receptor modulator compounds of present invention and the reference agonist and antagonist compounds shown in Table 1 on PR, AR, ER, GR and MR.

| Cmpd No. | PR Potency | | AR Potency | | ER Potency | | GR Potency | MR Potency |
|---|---|---|---|---|---|---|---|---|
| | Agon (nM) | Antag (nM) | Agon (nM) | Antag (nM) | Agon (nM) | Antag (nM) | Antag (nM) | Antag (nM) |
| Prog | 4 | na | 1300 | na | na | na | na | nt |
| RU486 | na | 0.1 | na | 12 | na | 1500 | 0.7 | 1100 |
| DHT | na | 1800 | 6 | na | 1700 | na | na | nt |
| Flut | na | 1900 | na | 26 | na | na | na | na |
| Estr | nt | nt | na | na | 7 | na | na | nt |
| ICI 164 | na | na | na | na | na | 160 | na | na |
| Spir | nt | 268 | nt | nt | na | na | 2000 | 25 | na = not active (i.e., efficacy of >20 and potency of >10,000);
nt = not tested

Pharmacological and Other Applications

As is discernible to those skilled in the art, the androgen receptor modulator compounds of the present invention may be readily utilized in pharmacological applications where AR antagonist or agonist activity is desired, and where it is desired to minimize cross reactivities with other steroid receptor related IRs. In vivo applications of the invention include administration of the disclosed compounds to mammalian subjects, and in particular to humans.

The following Example provides illustrative pharmaceutical composition formulations:

EXAMPLE 43

Hard gelatin capsules are prepared using the following ingredients:

| | Quantity (mg/capsule) |
|---|---|
| COMPOUND 101 | 140 |
| Starch, dried | 100 |
| Magnesium stearate | 10 |
| Total | 250 mg |

The above ingredients are mixed and filled into hard gelatin capsules in 250 mg quantities.

A tablet is prepared using the ingredients below:

| | Quantity (mg/tablet) |
|---|---|
| COMPOUND 101 | 140 |
| Cellulose, microcrystalline | 200 |
| Silicon dioxide, fumed | 10 |
| Stearic acid | 10 |
| Total | 360 mg |

The components are blended and compressed to form tablets each weighing 665 mg.

Tablets, each containing 60 mg of active ingredient, are made as follows:

| | Quantity (mg/tablet) |
|---|---|
| COMPOUND 101 | 60 |
| Starch | 45 |
| Cellulose, microcrystalline | 35 |
| Polyvinylpyrrolidone (PVP) (as 10% solution in water) | 4 |
| Sodium carboxymethyl starch (SCMS) | 4.5 |
| Magnesium stearate | 0.5 |
| Talc | 1.0 |
| Total | 150 mg |

The active ingredient, starch, and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate, and talc, previously passed through a No. 60 mesh U.S. sieve, and then added to the granules which, after mixing, are compressed on a tablet machine to yield tablets each weighing 150 mg.

Suppositories, each containing 225 mg of active ingredient, may be made as follows:

| | |
|---|---|
| COMPOUND 101 | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

An intravenous formulation may be prepared as follows:

| COMPOUND 101 | 100 mg |
|---|---|
| Isotonic saline | 1,000 mL |
| Glycerol | 100 mL |

The compound is dissolved in the glycerol and then the solution is slowly diluted with isotonic saline. The solution of the above ingredients is then administered intravenously at a rate of 1 mL per minute to a patient.

While in accordance with the patent statutes, description of the preferred embodiments and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following non-limiting enumerating embodiments.

What is claimed is:

1. A compound having the formula:

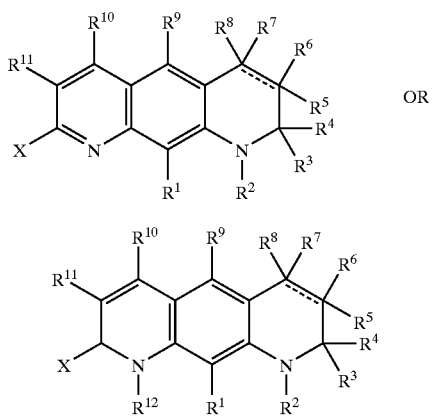

wherein:
$R^1$ is hydrogen;
$R^2$ is selected form the group of hydrogen, $C_1$–$C_6$ alkyl and $C_2$–$C_6$ alkenyl, wherein the $C_1$–$C_6$ alkyl and $C_2$–$C_6$ alkenyl groups are optionally substituted with $C_1$–$C_6$ alkyl, arylalkyl, or aryl;
$R^3$ and $R^4$ each independently is $C_1$–$C_6$ alkyl;
$R^5$ and $R^6$ each independently is selected from the group of hydrogen, $C_1$–$C_6$ alkyl, $C_1$–$C_6$ haloalkyl, $C_1$–$C_6$ perhaloalkyl, $C_2$–$C_6$ alkenyl, and $C_2$–$C_6$ alkynyl; or
$R^5$ and $R^6$ taken together form a =O;
$R^7$ and $R^8$ each independently is selected from the group of hydrogen, $C_1$–$C_6$ alkyl, $C_1$–$C_6$ haloalkyl, $C_1$–$C_6$ perhaloalkyl, $C_2$–$C_6$ alkenyl, and $C_2$–$C_6$ alkynyl; or
$R^7$ and $R^8$ taken together form a =O;
$R^9$ is hydrogen;
$R^{10}$ is selected from the group F, Cl, Br, $CF_3$, $CF_2OR^2$, $CH_2OR^2$, [$OR^2$,] and $C_1$–$C_6$ alkyl;
$R^{11}$ is selected from the group of hydrogen, F, Cl, Br, I, $C_1$–$C_6$ alkyl, $C_1$–$C_6$ haloalkyl, $C_1$–$C_6$ perhaloalkyl, $C_2$–$C_6$ alkenyl, $C_2$–$C_6$ alkynyl, and aryl, wherein the alkyl, haloalkyl, perhaloalkyl, alkenyl, alkynyl, and aryl, groups are optionally substituted with hydrogen, F, Cl, Br, $C_1$–$C_4$ alkyl, $OR^2$, $NR^{13}R^{14}$, or $SR^2$;
$R^{12}$ is selected from the group of hydrogen, $C(O)R^{11}$, $SR^2$, $S(O)R^{13}$, $S(O_2)R^{13}$, $C_1$–$C_6$ alkyl, $C_2$–$C_6$ alkenyl, aryl and benzyl, wherein the alkyl, alkenyl, aryl, and benzyl groups are optionally substituted with hydrogen, F, Cl, Br, $C_1$–$C_4$ alkyl, $OR^2$, $NR^{13}R^{14}$, or $SR^2$;
X is $S(O)R^{13}$;
$R^{13}$ is selected from the group of hydrogen, $C_1$–$C_6$ alkyl, $C_2$–$C_6$ alkenyl, $C_1$–$C_6$ haloalkyl, $C_1$–$C_6$ perhaloalkyl, aryl, and arylalkyl, wherein the alkyl, alkenyl, haloalkyl, perhaloalkyl, aryl, and arylalkyl groups are optionally substituted with hydrogen, F, Cl, Br, $C_1$–$C_4$ alkyl, $OR^2$, $NR^{13}R^{14}$, or $SR^2$;
$R^{14}$ each independently is selected from the group of hydrogen $C_1$–$C_6$ alkyl, $C_2$–$C_6$ alkenyl, $C_1$–$C_6$ haloalkyl, $C_1$–$C_6$ perhaloalkyl, aryl, and arylalkyl, wherein the alkyl, alkenyl, haloalkyl, perhaloalkyl, aryl, and arylalkyl groups are optionally substituted with hydrogen, F, Cl, Br, $C_1$–$C_4$ alkyl, $OR^2$, $NR^{13}R^{14}$, or $SR^2$;
with the proviso that when the dotted line in the ring structure is a double bond, $R^6$ and $R^7$ are absent;
or a pharmaceutically acceptable salts thereof.

2. A compound according to claim 1, wherein $R^{10}$ is selected from the group of F, Cl, Br, $CF_3$, $CF_2OR^2$, $CH_2OR^2$, $OR^2$, and $C_1$–$C_6$ alkyl.

3. A compound according to claim 2, wherein $R^{10}$ is selected from the group of F, Cl, Br, and $CF_3$.

4. A compound according to claim 1, wherein $R^2$ is selected from the group of hydrogen and $C_1$–$C_4$ alkyl.

5. A compound according to claim 1, wherein $R^5$ and $R^8$ each independently is selected from the group of hydrogen, $C_1$–$C_6$ alkyl, and $C_1$–$C_6$ perhaloalkyl, $C_2$–$C_6$ alkenyl, and $C_2$–$C_6$ alkynyl.

6. A compound according to claim 5, wherein $R^5$ and $R^8$ each independently is selected from the group of hydrogen and $C_1$–$C_6$ alkyl.

7. A compound according to claim 1, wherein $R^{11}$ is selected from the group of hydrogen, $C_1$–$C_4$ alkyl, F, Cl, and Br.

8. A compound according to claim 7, wherein $R^{11}$ is selected from the group of hydrogen, F, Cl, and Br.

9. A compound according to claim 1, wherein $R^{12}$ is selected from the group of hydrogen, $C_1$–$C_6$ alkyl, $C_3$–$C_6$ allyl, and benzyl, and wherein the alkyl, allyl and benzyl groups are optionally substituted with hydrogen, F, Cl, Br, $C_1$–$C_4$ alkyl, $OR^2$, $NR^{13}R^{14}$ and $SR^2$.

10. A compound according to claim 1, wherein $R^{13}$ and $R^{14}$ each independently is selected from the group of hydrogen and $C_1$–$C_6$ alkyl.

11. A compound according to claim 1, wherein $R^6$ and $R^7$ each independently is selected from the group of hydrogen, $C_1$–$C_6$ alkyl, $C_1$–$C_6$ perhaloalkyl and nothing.

12. A compound according to claim 11, wherein $R^6$ and $R^7$ are hydrogen.

13. A compound according to claim 1, wherein:
$R^2$ and $R^5$ each independently is hydrogen or $C_1$–$C_6$ alkyl;
$R^6$ and $R^7$ are each hydrogen;
$R^8$ is hydrogen or $C_1$–$C_6$ alkyl;
$R^{10}$ is selected from the group of F, Cl, Br, and $CF_3$;
$R^{11}$ is selected from the group of hydrogen, F, Cl, and Br; and
$R^{12}$ is hydrogen.

14. A compound according to claim 1, wherein:

$R^2$ and $R^8$ each independently is hydrogen or $C_1$–$C_6$ alkyl;

$R^5$, $R^6$, and $R^7$ are each hydrogen;

$R^{10}$ is $CF_3$; and $R^{11}$ is hydrogen or F.

15. A compound according to claim 1, wherein said compound is selected from the group of (R/S)-1,2,3,4-Tetrahydro-2,2-dimethyl-8-methylsulfinyl-6-trifluoromethyl-9-pyrido[3,2-g]quinoline; 1,2,3,4-Tetrahydro-2,2-dimethyl-8-methylsulfonyl-6-trifluoromethyl-9-pyrido[3,2-g]quinoline; (R/S)-7-Fluoro-1,2,3,4-tetrahydro-2,2-dimethyl-6-trifluoromethyl-8-methylsulfinyl-9-pyrido[3,2-g]quinoline; (R/S)-1,2,3,4-Tetrahydro-2,2-dimethyl-8-(1-n-butylsulfinyl)-6-trifluoromethyl-9-pyrido[3,2-g]quinoline; (R/S)-4-Ethyl-1,2,3,4-tetrahydro-8-methylsulfinyl-6-trifluoromethyl-9-pyrido[3,2-g]quinoline; and 1,2,3,4-Tetrahydro-8-bis(methanesulfon)amido-2,2-dimethyl-6-trifluoromethyl-9-pyrido[3,2-g]quinoline.

16. A pharmaceutical composition comprising a compound according to claim 15 and a pharmaceutically acceptable carrier, wherein the composition is formulated for oral, topical, intravenous, suppository or parenteral administration.

17. A pharmaceutical composition comprising a compound of claim 1 and a pharmaceutically acceptable carrier.

18. A pharmaceutical composition according to claim 17, wherein the composition is effective as an anabolic agent.

19. A method of treating a patient susceptible to androgen receptor therapy comprising administering to said patient an effective amount of a compound according to claim 1.

* * * * *